United States Patent [19]
Dorner et al.

[11] Patent Number: 6,165,711
[45] Date of Patent: Dec. 26, 2000

[54] PROCESS FOR DISINTEGRATING NUCLEIC ACIDS AND PREPARING BIOLOGICAL PRODUCTS OF GUARANTEED QUALITY

[75] Inventors: Friedrich Dorner, Vienna; Noel Barrett, Klosterneuburg/Weidling; Johann Eibl, Vienna, all of Austria

[73] Assignee: Baxter Aktiengesellschaft, Vienna, Austria

[21] Appl. No.: 09/155,758

[22] PCT Filed: Apr. 8, 1997

[86] PCT No.: PCT/AT97/00068

§ 371 Date: Nov. 18, 1998

§ 102(e) Date: Nov. 18, 1998

[87] PCT Pub. No.: WO97/37686

PCT Pub. Date: Oct. 16, 1997

[30] Foreign Application Priority Data

Apr. 9, 1996 [AT]  Austria ........................... 629/96

[51] Int. Cl.[7] .............. C12Q 1/70; C12Q 1/68; C12N 5/00; A01N 63/00
[52] U.S. Cl. ................ 435/5; 435/6; 435/325; 424/93.1
[58] Field of Search .................. 435/5, 6, 325; 424/93.1

[56] References Cited

U.S. PATENT DOCUMENTS

| | | | |
|---|---|---|---|
| 4,950,665 | 8/1990 | Floyd | 514/228.8 |
| 5,571,666 | 11/1996 | Floyd et al. | 435/2 |
| 5,827,644 | 10/1998 | Floyd et al. | 435/2 |

FOREIGN PATENT DOCUMENTS

| | | |
|---|---|---|
| 389889B | 2/1990 | Austria . |
| 2150044 | 3/1996 | Canada . |
| 3505728A1 | 9/1985 | Denmark . |
| 4403798A1 | 8/1995 | Denmark . |
| 0152072A2 | 8/1985 | European Pat. Off. . |
| 0196515A1 | 10/1986 | European Pat. Off. . |
| 4-131085 | 5/1992 | Japan . |
| WO90/13296 | 11/1990 | WIPO . |
| WO91/03933 | 4/1991 | WIPO . |
| WO91/16911 | 11/1991 | WIPO . |
| WO96/20592 | 7/1996 | WIPO . |

OTHER PUBLICATIONS

Baba et al. Biochemical and Biophysical Research Communications 155(3): 1404–1411 (1998).
Badylak et al. Journal of Clinical Microbiology 17(2): 374–376 (1983).
Balzarini et al. Int. J. Cancer 37: 451–457 (1986).
Cadet et al. Israel Journal of Chemistry 23: 420–429 (1983).
Darzynkiewicz et al. Cancer Research 48: 1295–1299 (1988).
Edelson et al. The New England Journal of Medicine 316(6): 297–303 (1987).
Floyd et al. Archives of Biochemistry and Biophysics 273(1): 106–111 (1989).
Friedman et al. Nucleic Acids Research 5(2): 615–622 (1978).
Gasparro et al. Biochemical and Biophysical Research Communications 141(2): 502–509 (1986).
Gerba et al. Photochemistry and Photobiology 26: 499–504 (1977).
Heinmets et al. Memorandum Report, Naval Medical Research Institute, National Naval Medical Center vol. 10, pp. 571–578 (Nov. 1952).

(List continued on next page.)

*Primary Examiner*—Hankyel Park
*Attorney, Agent, or Firm*—Foley & Lardner

[57] ABSTRACT

The invention relates to a method for the disintegration of any biologically active nucleic acid in a biological material, wherein a biologically active material is exposed or multiply exposed to laser beam to disintegrate essentially all biologically active nucleic acid in said biological material, while the biological integrity and activity of said biological material is maintained.

60 Claims, 1 Drawing Sheet

OTHER PUBLICATIONS

Heinmets et al. Walter Reed Army Institute of Research, Walter Reed Army Medical Center, Wrair–53–55 (Nov. 1955).

Inada et al. Biochimica et Biophysica Acta 532: 161–170 (1978).

Korhauser et al. Photochemistry and Photobiology 18: 63–69 (1973).

Lambrecht et al. Vox Sang 60: 207–213 (1991).

Matthews et al. Transfusion 28(1): 81–83 (1988).

Sastry et al. Biochimica et Biophsica Acta 129: 32–41 (1966).

Simon et al. Archives of Biochemistry and Biophysica 105: 197–206 (1964).

Swartz et al. Proceedings of the Society for Biology and Medicine 161: 204–209 (1979).

Sinkovics et al. Cancer Research 25: 624–627 (1965).

Thormar et al. Acta Path. et Microbial. Scandinav. 62, 461–462 (1964).

Waskell et al. Biochimica et Biophsica Acta 129: 49–53 (1966).

PROCESS FOR DISINTEGRATING NUCLEIC ACIDS AND PREPARING BIOLOGICAL PRODUCTS OF GUARANTEED QUALITY

BACKGROUND OF THE INVENTION

1. Field of the Invention

The present invention relates to the disintegration of biologically active nucleic acids in a biologically active material by exposing the biological material, optionally treated with a photodynamic substance, to a laser beam which yields a non-infectious biological product having essentially all biologically active nucleic acid disintegrated while the biological integrity and activity, such as antigenicity, immunogenicity, protectivity or enzymatic characteristics, of the biological material is maintained. The invention relates also to the production of biologicals, such as vaccines, genetically engineered protein products, monoclonal antibodies or blood factors having essentially all biologically active nucleic acid disintegrated.

The use of continuous cell lines (CCL) for the production of therapeutic biological products and the problems of contaminating nucleic acids in biological products as well as the inactivation of residual contaminating cellular DNA in such biologicals have been discussed. While certain products, such as recombinant proteins, vaccines or monoclonal antibodies, are effectively produced using vertebrate cells, certain other protein products are not easily obtained from common used cells due to the low production rate of the proteins in those cells. Other mammalian cells which are easy to cultivate are not licensed by regulatory authorities for the production of genetically engineered proteins and for their use for therapeutic and prophylactic porposes in humans or animals.

It has been suggested to use mammalian cell lines for the genetically engineered manufacture of many proteinaceous products as well as for the production of virus vaccines. However, certain problems are anticipated in the use of such cell lines. Many products are not released or secreted from mammalian cells directly into the culture medium. Accordingly, the harvest of such products often will require rupturing cellular membranes to release those products into the medium from which they may subsequently be refined or purified. Such rupture, however, will also release cellular nucleic acid into the medium. Particularly because many easily cultured cell lines are transformed mammalian tumorogenic cell lines with an oncogenic potential, such as MDCK cells or SK-Hep cells, a need exists to ensure that active nucleic acid is not present as a contaminant in the proteinaceous end product or in the vaccine preparation. Attempts, therefore, have been made to inactivate cellular nucleic acids that might be associated with a risk of oncogenicity.

Vaccination against viral diseases has been one of the major tasks of medicine over the past century. While effective vaccines have been developed for a large number of diseases, development of safe and effective vaccines for a number of other diseases, e.g. HIV infections, remain problematic. The use of inactivated or killed viral agents as a vaccine, although generally safe, will not always be effective if the immunogenic characteristics of the agent are altered. However, if a highly infectious, virulent virus is used for vaccine manufacture, one has to be sure that the inactivation process results in a total loss of infectivity.

The use of live, attenuated viral agents as vaccines will often result in improved immunologic reactivity, but increases the risk associated with vaccination in that the vaccine itself is infectious. For example, the virus may revert to an active, virulent form and the organism may be able to propagate and disseminate leading to disease.

Thus, one must generally choose between improved effectiveness and greater degree of safety when selecting between live attenuated and inactivated vaccine preparations. The choice is particularly difficult when the virus is resistant to inactivation processes and requires highly rigorous inactivation conditions which are likely to negatively affect the antigenic characteristics.

Various techniques are known for killing or inactivating viruses for vaccine use. These include chemical or physical treatment e. g. inactivation with formaldehyde, hydroxylamine, $\beta$-propiolactone, UV irradiation, or photodynamic dyes, e.g. methylene blue and visible light. Despite these general disclosures, a need exists to improve the selectivity of such inactivation methods such that protein viral coats will better retain their integrities while inactivation/kill rates are enhanced.

One major problem of inactivated virus vaccines is that if the inactivation process of the viral nucleic acid is not complete, there is the risk that virus nucleic acid may be administered to a host associated with the virus vaccine, and under certain circumstances this may itself be infectious. E.g. HIV RNA could be reverse transcribed by viral or cellular enzymes and be integrated into the host genome, leading to HIV replication.

Many attempts have been made to inactivate viruses in a sample, such as vaccines or plasma, or cellular nucleic acids while preserving the antigenic and immunogenic properties of the proteins in that sample.

2. Description of Related Art

U.S. Pat. No. 5,106,619 discloses a viral vaccine with preserved antigenic and immunogenic characteristics produced by inactivation of enveloped and non-enveloped viruses with UV light in the presence of fourocoumarin in a non-oxidizing atmosphere.

U.S. Pat. No. 4,880,512 discloses a method for treating biological media such as blood fractions, genetically engineered protein products and vaccine preparations and the photolysis of nucleic acids in the presence of proteins, while preserving the antigenic and immunogenic properties of the protein. Biological media comprising tryptophan-containing proteins were irradiated with pulsed light of different wavelengths and flux.

Matthews et al. (1992, Blood Cells 18:75–89) reported about inactivation of viruses in virus-infected cells in culture media or in whole blood by irradiation with filtered xenon light source and/or a tuneable dye laser in the presence of a photodynamic dye. Prodouz et al. (1987, Blood 70:589–592) disclosed a method for virus inactivation in samples by UV irradiation using a radiation at 308 nm of XeX1 eximer laser. In WO 96/00091 samples are irradiated with electromagnetic radiation generated by a tuneable laser-device at a wavelength in the range of from 300 to 370 nm for virus inactivation.

Perrin et al. (1995, Biologicals 23:207–211) used $\beta$-propionlactone for the inactivation of residual contaminating cell DNA in biologicals. Although this agent is known to inactivate viruses, its use is difficult to control because of the lability and reactivity of the agent. It rapidly hydrolyses in aqueous solutions and it can also modify the product e.g. by reducing Fc function in immunoglobulins.

The use of nucleases to inactivate DNA or RNA has also been suggested, but it is known that this is not a very effective procedure in that a high percentage of nucleic acid may be associated with protein and thus be inaccessible to nucleases.

It is known that photosensitive dyes and, in particular phenothiazine dyes, such as methylene blue, bengal rose, neutral red or toluidine blue, in the presence of light or UV light can inactivate viruses. This is caused by the preferred affinity of the photodyes to nucleic acids.

The reactivity of phenothiazine dye with viruses has been studied since 1930. Perdrau et al. (1933, Proc. Roy. Soc. 122:288–298) reported that a wide range of viruses can be inactivated by the action of methylene blue in the presence of light. Rabiesvirus, influenza virus, Juninvirus, canine distemper virus, HIV and herpes simplex virus were shown to be inactivated by methylene blue and light irradiation (Swartz et al., 1979, Proc. Soc. Exp. Biol. Med., 161:204–209; Schnipper et al., 1980, J. Clin. Invest., 65:432–438; Cobo et al., 1986, Med. Microbiol. Immunol., 175:67–69, Bachmann et al.,1995, J. Med.Virol. 47:172–178). Enveloped viruses, in general, possess some inherent photosensitivity, while non-enveloped viruses are photoresistant (Wallis et al., 1964, Virology 23:520–527).

EP 0 196 515 discloses a method for inactivation of viruses in a therapeutic protein composition by exposing the composition to light in the presence of a photosensitizer. Preferred photosensitizers used were protoporphyrin and chlorpromazine. It was found that viruses could be inactivated, but that under the conditions tested some inactivation of Factor VIII also occurs.

U.S. Pat. No. 4,181,128 discloses a system for inactivation of microorganisms, such as viruses, bacteria, toxins and tumor cells by treatment with methylene blue, light, electricity and an oxygen atmosphere.

U.S. Pat. No. 4,950,665 discloses a method for using methylene blue to selectively derivatize guanosine and to inactivate virus and cancerous cells in vivo.

Treatment of plasma with methylene blue and light leads to inactivation of enveloped viruses including HIV, HSV, VSV and some non-enveloped viruses such as SV40 (Mohr et al., 1992, Ann. Hematol. 65:224–228). Although it is believed that nucleic acids are the preferred targets of methylene blue/light treatment (Tuite et al., 1993, Photochem. Photobiol. B: Biol. 21:103–124), some alterations in capsid proteins of methylene blue-photoinactivated viruses as well as a loss of the activity of plasma proteins has been observed (Specht et al., 1994, Photochem. Photobiol. 59:506–514; Bachmann et al., 1995, J. Med. Virol. 47:172–178, Mohr et al., 1995, Immunol. Invest. 24:73–85).

SUMMARY OF THE INVENTION

It is apparent, therefore, that an improved method for the inactivation of nucleic acids in biologicals has to be developed that reduces the risk of a residual contamination of active nucleic acid in a biological while preserving the biological integrity and activity of proteinaceous products in that sample.

It is an object of the present invention to provide an improved method for the disintegration of nucleic acids in a biological material.

It is another object of the present invention to provide a method for the production of a safe biological material having essentially all biologically active nucleic acid disintegrated, while the biological integrity and activity of the proteinaceous material is maintained.

It is a further object of the present invention to provide for safe biologicals, such as recombinant proteins, monoclonal antibodies, vaccines or blood derivatives.

In achieving these objects, there has been provided with one aspect of the present invention, a method for the disintegration of any biologically active nucleic acid in a biological material, wherein a biologically active material is exposed or multiple exposed to a laser beam to disintegrate essentially all biologically active nucleic acid in the biological material, while the biological integrity and activity of the biological material is maintained.

According to one aspect of the method prior to the exposure of the biological material to laser beam a photodynamic substance may be added, wherein the photodynamic substance is a substance that can be activated by laser beams.

In a preferred embodiment of the method of the present invention prior to exposure of the biologically active material to a laser beam a stabiliser and/or a quencher and/or scavenger is added.

According to the method of the invention the biologically active material comprises a high molecular weight biologically active substance other than a biologically active nucleic acid.

According to the method of the invention the biologically active nucleic acid that is disintegrated by the method of the invention is DNA or RNA.

In accordance with another aspect of the invention, there has been provided a method for disintegration of a biologically active nucleic acid in a virus-containing biological material, wherein a virus-containing biologically active material is exposed to a laser beam to disintegrate essentially all biologically active nucleic acid in the biological material, while the biological integrity and activity, such as antigenicity, immunogenicity and protectivity, of the virus in the biological material is maintained. Prior to an exposure to a laser beam, a photodynamic substance may be added to the biological material.

In another preferred embodiment of the method the virus-containing biological material is derived from a culture of virus-infected cells, a culture supernatant of virus-infected cells, a cell component of virus-infected cells or a solution comprising a purified virus.

According to another aspect of the invention the method is used for the production of an inactivated virus. Preferably, the virus is a lipid-(enveloped) or a non-lipid (non-enveloped) virus, a DNA or a RNA virus, or an attenuated virus.

In accordance with another aspect of the invention there is provided an inactivated virus obtained by exposing a virus containing solution to laser beam, said inactivated virus containing a disintegrated biologically active nucleic acid, while its biological integrity and activity, such as antigenic, immunogenic and protective property, is maintained. The inactivated virus with the properties described above can be any type of virus, such as a lipid-(enveloped) or a non-lipid (non-enveloped) virus, a DNA or an RNA virus, or an attenuated virus.

According to another aspect of the invention the inactivated virus is formulated into a vaccine preparation.

In accordance with another aspect of the invention there is provided a vaccine comprising an inactivated virus, wherein in the inactivated virus all biologically active nucleic acid has been disintegrated, while its biological integrity and activity, such as antigenicity, immunogenicity and protectivity, are maintained. Optionally, the vaccine preparation comprises a physiologically acceptable carrier.

In another aspect of the invention there is provided a method for disintegration of a biologically active nucleic acid in a biological material comprising a genetically engineered proteinaceous product, wherein the biologically active material is exposed to a laser beam to disintegrate essentially all biologically active nucleic acid in the material, while the biological integrity and activity of the genetically engineered proteinaceous product is maintained.

In accordance with another aspect of the invention, there is provided a method for the disintegration of a biologically active nucleic acid in a microorganism-containing biological material, wherein a microorganism-containing biologically active material is exposed to a laser beam to disintegrate essentially all biologically active nucleic acid in the biological material, while the biological integrity and activity, such as antigenicity, immunogenicity and protectivity, of the microorganism in the biological material is maintained.

In accordance with another aspect of the invention, there is provided a method for the production of an inactivated microbiological vaccine.

In accordance with another aspect of the invention there is provided a biologically active material having been exposed to a laser beam, wherein all the biologically active nucleic acid of the biological material has been disintegrated, while its biological integrity and activity, such as antigenic, immunogenic and protective properties, are maintained.

In accordance with another aspect of the invention there is provided a biologically active material having been treated with a photodynamic substance and exposed to a laser beam.

In accordance with another aspect of the invention there is provided a pharmaceutical preparation comprising a biological material as described above and a pharmaceutically acceptable carrier. The pharmaceutical preparation of the present invention can be used for the treatment of a mammal.

Other objects, features and advantages of the present invention will become apparent from the following description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF ASPECTS OF THE INVENTION

Figure 1:
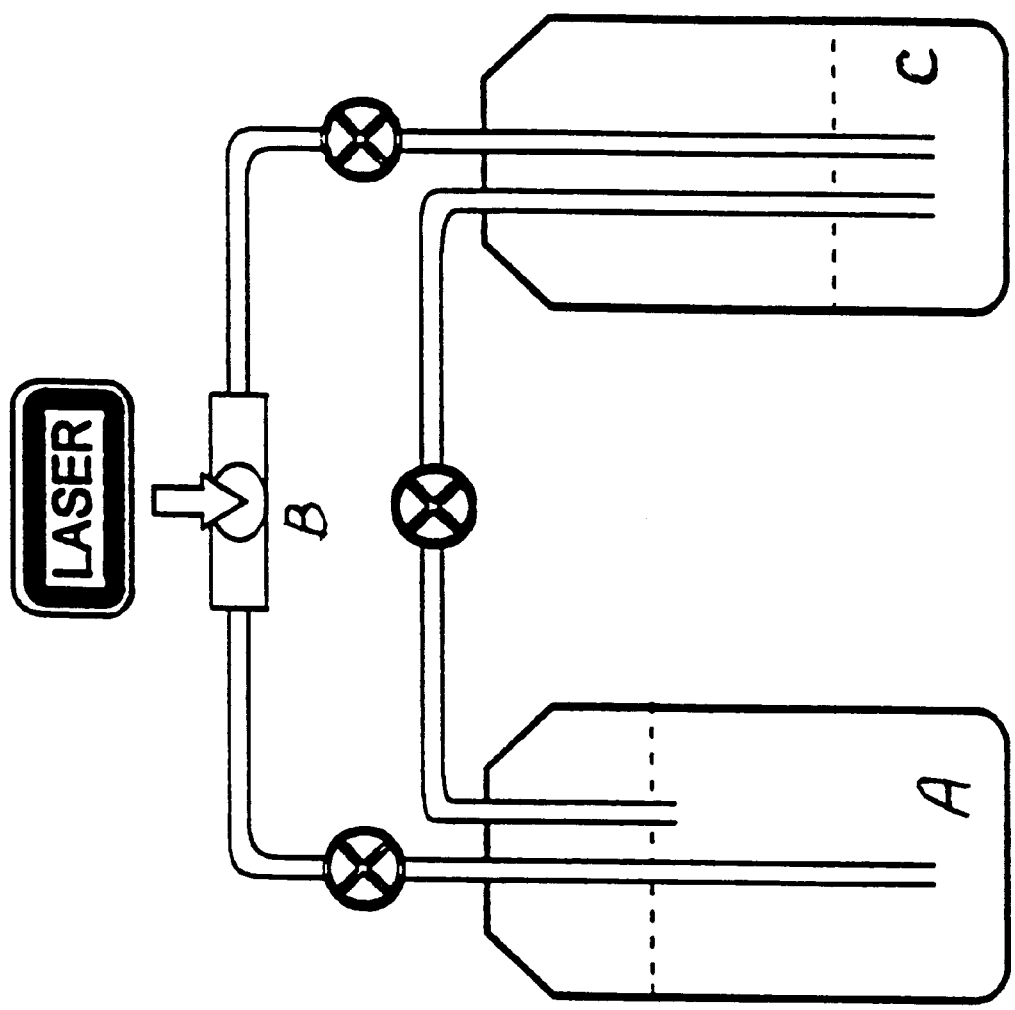

The present invention provides for a new method for the disintegration of biologically active nucleic acids in a biologically active material. "Biologically active material" means a material comprising biologically active proteinaceous products contaminated by undesired nucleic acid, either derived from a cell, cell culture line, a virus, a nucleic acid vector, a prokaryotic or eukaryotic pathogen or an oncogene. "Disintegration" of a nucleic acid means the destruction of the nucleic acid entities and activity in the presence of proteins to cause loss of the viability and infectivity of the nucleic acid, while substantially maintaining the functionality and biological integrity and activity of the protein present in the biological material. An object of the present invention is to disintegrate essentially all biologically active nucleic acids, such as DNA or RNA, including infectious nucleic acid molecules capable of transformation which are suspected to be in the biological material, while leaving the integrity and activity of the proteins in the biological material intact. The material comprising a biologically active protein obtained after the disintegration process has essentially all biologically active nucleic acids disintegrated. "Essentially" means that the residual active nucleic acid in the biological material is below the detection level of a highly sensitive nucleic acid amplification method.

According to method of the present invention the amount of residual contaminating genomic DNA and/or viral active nucleic acid, RNA or DNA, is determined after the disintegration or inactivation process. This determination is particularly important when determining the contaminating active nucleic acid in blood products, vaccines or in the quality control of recombinant products derived from cell cultures. The efficiency of disintegration can be measured by determining the residual nucleic acid by a nucleic acid amplification method, such as ligase chain reaction (LCR), nucleic acid sequence based amplification (NASBA), self-sustained sequence replication (3SR), transcriptional based amplification system (TAS) or polymerase-chain reaction (PCR). In a preferred embodiment of the method of the invention the amplification method is PCR.

In order either to determine quantitatively the nucleic acid in a sample the LIF-PCR (laser induced flourescence PCR) is preferably used. By using non-radioactively-labeled primers (preferably, primers labeled with a flourescent dye are used) the PCR products can be detected by LIF-PCR. In the case of LIF-PCR, the nucleic acid is amplified in the presence of flourescence labeled primers and the amplification products are subsequently separated by PAGE. The amplification is carried out with primers specific for the respective nucleic acid of the microbiological or molecular pathogen or the contaminating genomic DNA.

In order to quantify the efficiency of the inactivation and disintegration method prior to the amplification a given amount of a known nucleic acid is added to the sample as an internal standard, wherein the standard nucleic acid differs from the genomic or viral nucleic acid to be determined in at least one detectable characteristic, yet it should be capable of being amplified by aid of the same primer.

Until the present invention it has not been possible to completely disintegrate biologically active nucleic acids in a biological sample without substantially negatively affecting the biological activity and/or integrity of proteins present in the sample. It also has not been possible to determine and quantify the efficiency of the nucleic acid disintegration process by PCR amplification methods to have a reproducible system for the production of safe and quality-controlled biologicals.

According to the present invention there has been provided with one aspect of the present invention, a method for the disintegration of any biologically active nucleic acid in a biological material, wherein a biologically active material is exposed or multiple exposed to a laser beam to disintegrate essentially all biologically active nucleic acid in the biological material, while the biological integrity and activity of the biological material is maintained.

According to one aspect of the method prior to the exposure of the biological material to laser beam a photodynamic substance can be added, wherein the photodynamic substance is a substance that can be activated by laser beams. Preferably, the photodynamic substance adsorbs light in the wavelength range of the laser beam or above, wherein the wavelength of the laser beam used is the wavelength of the maximal activation rate of the photodynamic substance. The wavelength of the laser beam used is preferably between 600 and 680 nm, in particular between 630 and 660 nm.

All known laser devices, e.g. a Xenon laser, a He-Ne laser or a YAG laser, can be used for carrying out the method, a He-Ne laser, however, being preferred. In doing so, a system is used in which the biological material is passed through a tube or a cuvette having a glass window, and the glass window is irradiated with the laser beam.

The energy density acting on the biological material is determined by the applied radiation intensity of the laser in dependence on the dwell time of the liquid in the laser beam region (mWs/mm$^2$ or mJ/mm$^2$). The radiation intensity of the laser is the laser output per laser radiation area (mW/mm$^2$). The dwell time in the beam depends on the geometry of the glass window (diameter×length) and on the flow rate (ml/min).

The laser output used preferably is in a range of between 1 mW and 20 mW. When carrying out this method, the maximum laser intensity per cycle should be <0.1 J/cm$^2$, in particular $\leq 0.08$ J/cm$^2$, depending on the radiation intensity of the laser and the dwell time of the biological material under the action of the radiation of the laser. According to the method of the invention, irradiation with the laser is effected with an energy density preferably in a range of between 0.001 J/cm$^2$ up to 0.1 J/cm$^2$ at the most, particularly preferred between 0.006 J/cm$^2$ and 0.06 J/cm$^2$.

In case a single photodynamic substance is added to the material, the material is preferably irradiated with a laser beam of one selected wavelength. If more than one photodynamic substance is added to the biological material the material is irradiated with different wavelengths of laser beam, wherein the wavelengths chosen are selected from the maximal activation rate of the photodynamic substances used. The photodynamic substance added is preferably in a concentration between 0.01 $\mu$M and 50 $\mu$M, preferably between 10 $\mu$M and 35 $\mu$M. The photodynamic substance is preferably selected from the group of photodynamic dyes such as the phenothiazines methylene blue, neutral red, toluidine blue, azure blue, bengal red, macrocyclic or heterocyclic photosensitizers such as benzophorphyrin or derivatives thereof or other photoactive substances well known in the art. The photodynamic substance is usually dissolved in a solution which allows the complete dissolution of the substance when combined with the biological material. The photodynamic substance can be added to the biological material in the dark and the mixture is then pumped through a system with a window for the exposure to laser beam for a time sufficient to disintegrate essentially all biologically active nucleic acid in that biological material. In order to preserve the biological activity and integrity of the biological, laser beam irradiation is carried out within a time sufficient to disintegrate all biologically active nucleic acid without netatively affecting the biological integrity and activity of a proteinaceous material. The parameters for disintegration are the diameter of the laser beam, the diameter of the window through which the biological is irradiated, the flow rate with which the substance is pumped through the window, the exposure time, the wavelength of the laser beam, optionally the concentration of the photodynamic substance and the concentration of the nucleic acid in the material. According to one aspect of the invention the method can be performed in a buffered system in a pH range between 5 and 10 and at a temperature between 4° C. and 35° C., depending on the photodynamic substance added, but under optimal conditions to disintegrate the nucleic acid while the biological integrity and activity of the biologically active material is maintained. Preferably, the temperature, pH and ionic strength conditions chosen for nucleic acid disintegration are kept stable for the entire duration of the process. Parameters relevant to the inactivation are optimized for each biological material.

When the exposure to laser beam or the photodynamic substance/laser beam treatment is used to disintegrate. biologically active nucleic acid of microbiological or molecularbiological pathogens in blood, plasma, serum, a cell suspension, a cell layer, a cell supernatant or a broken-up cell preparation derived from infected, transfected or transformed cell a stabilizer, such as sugars, polyalcohols, amino acids, peptides or carboxylic acids, a quencher and/or scavenger such, as mannitol, glycerol, reduced glutathione or superoxide dismutase, or a combination thereof may be added to biological material prior to laser beam exposure or addition of a photodynamic substance. According to the method there may be also added to the biological material prior to exposure to laser beam one or more different quenchers and/or scavengers and/or stabilizers. The addition of quenchers of type I photodynamic reactions (free radicals) such as mannitol, glycerol, reduced glutathione (GSH), or superoxide dismutase (SOD) can allow the use of high light intensities or energy intensity (>0.1 J/cm$^2$) and concentration of e.g. photodynamic substances without increased losses in activity, integrity, antigenicity, immunogenicity or enzmatic activity of a biological. This is due to the fact that a type II reaction (singlet oxygen) is the main mediator of nucleic acid inactivation, while both type I and II reactions contribute to protein inactivation. This is of particular importance for the use of this procedure for the inactivation of viruses in whole blood, plasma or plasma products and/or disintegration of viral and genomic nucleic acid in biological material without inducing losses of the activity and integrity of specific proteins of therapeutic importance.

Under the conditions used for disintegration of active nucleic acids it has been found that already low light or energy intensities can be used to inactivate even the most resistant viruses without destroying the biological activity and integrity of the blood factors or plasma proteins.

The disintegration of nucleic acids, in particular of non-enveloped viruses, and thus their inactivation has been particularly surprising with a view to the known prior art, since non-enveloped viruses, such as polio virus, HAV or parvovirus are considered to be photoresistant (Wallis et al., 1964, Virology 23:520–527; Mohr et al., 1995, Immunol. Invest. 24:73–85). By using a combination of photoactive substance and laser beam treatment at low energy density, the method according to the invention surprisingly also allows the inactivation of non-enveloped viruses in a biological material, such as plasma, or in the production of a vaccine containing, e.g., inactivated polio virus, HAV or parvovirus, it being ensured in the biological material that the integrity and biological activity of the proteins are maintained by the inactivation method.

In another preferred embodiment of the method prior to exposure to laser beam one or more photodynamic substances), at least one quencher and/or scavenger and/or stabilizer is (are) added and the mixture is irradiated with one or more different wavelength(s) of laser beam, wherein the wavelength of laser beam is the wavelength of the maximal activation rate of the photodynamic substance(s) added.

The photodynamic substance and/or quencher and/or scavenger and/or stabilizer can be added to a container comprising the biologically active material and the mixture of the photodynamic substance(s) and the biologically active material is pumped through a system for exposure to laser beam. In a preferred embodiment of the method the mixture exposed to laser beam is pumped directly to a second container. The mixture exposed to laser beam may be pumped back in the reverse direction through the system for at least a second laser irradiation. In another preferred embodiment of the method to the mixture in the second container at least a second portion of one or more photodynamic substance(s) and /or quencher and/or scavenger and/or stabilizer may be added and the mixture is pumped back in the reverse direction through the system for at least a second laser beam. The additives may be added to the mixture in a single addition or in multiple additions, the mixture being exposed to the laser beam in between the additions, or may be added continuously during the entirely treatment period. Usually the number of additions will be 1. According to the present invention this can be done by recycling the laser beam treated mixture of biological material and additives in a continuous process. The process can be repeated for several cycles, preferably 5 to 50 cycles, most preferably 10 to 30 cycles of laser beam treatment.

According to one aspect of the method the biologically active material comprises a high molecular weight biologically active substance other than a biologically active nucleic acid. Preferably, the biologically active material is a solution comprising a blood factor, a plasma factor, an immunoglobulin, a genetically engineered proteinaceous product, such as a recombinant protein or a monoclonal antibody or a microbiological and/or molecular pathogen, such as a virus or a bacterium, or a part thereof. In a preferred embodiment of the method the biological material comprises a proteinaceous product. Preferrably the material is selected from a solution comprising a blood factor, such as Factor II, Factor V, Factor VII, Factor VIII, Factor IX, Factor X, Factor XI, Factor XIII, Protein C, Protein S, von Willebrand Factor or a plasma protein, such as plasminogen, plasminogen activator inhibitor, antithrombin III, C1-esterase inhibitor, albumin, fibrinogen, γ-globulin, immunoglobulin, a genetically engineered protein product, such as a recombinant protein or a monoclonal antibody, or a pathogen, such as a virus or a bacteria. The biologically active material can be whole blood, a blood component or a derivative thereof, such as a plasma fraction, a plasma protein comprising a nucleic acid in form of a potential microbiological or molecular pathogen, a cell suspension, a cell layer, a cell culture supernatant or a broken-up cell preparation derived from infected, transfected or transformed cells or a cell culture comprising a contaminating biologically active nucleic acid.

The method of the present invention is suitable to disintegrate biologically active nucleic acid and inactivate viral pathogens such as HIV-1, HIV-2, HAV, HCV, HBV, parvovirus, CMV, HHV-6, HTLV-1, HTLV-2, EBV, HDV, echovirus and coxsackievirus in plasma or a plasma fraction.

Cells in that cell culture, cell suspension, cell layer, cell culture supernatant or in the broken-up cell preparation may be derived from vertebrate cells such as VERO cells, CHO cells, BHK cells, chicken embryo cells, MDCK cells, CV-1 cells, LLC-MK2 cells, MDBK cells, WI-38 cells, MRC-5 cells, SK-Hep cells or another continous cell line, such as a tumor cell line or a hybridoma cell line.

In one preferred embodiment of the invention the biologically active material is used for a vaccine preparation.

The biologically active nucleic acid that is disintegrated by the method of the invention is DNA or RNA. The nucleic acid may be a genomic DNA from a genome or a part thereof, such as a gene. The intact nucleic acid has a nucleic acid template activity and includes a sequence for primer and polymerase binding. It is also amplifiable by a nucleic acid amplification method. The nucleic acid can be derived from a eukaryotic source such as a vertebrate cell, a tumor cell line or a hybridoma cell line, from a microorganism, such as a protoza, a bacterium, a virus, a microbiological or molecular pathogen, or a part thereof, or from an oncogene or a protooncogene.

In accordance with another aspect of the invention, there has been provided a method for disintegration of a biologically active nucleic acid in a virus-containing biological material, wherein a virus-containing biologically active material is exposed to laser beam to disintegrate essentially all biologically active nucleic acid in the biological material, while the biological integrity and activity, such as antigenicity, immunogenicity and protectivity, of the virus in the biological material are maintained.

In a preferred embodiment of the method prior to exposure to laser beam a photodynamic substance can be added to the biological material.

In another preferred embodiment of the method the virus-containing biological material is derived from a culture of virus-infected cells, a culture supernatant of virus-infected cells, a cell component of virus-infected cells or a solution comprising a purified virus. The cells for propagating the virus are virus-infected cells preferably vertebrate cells including cells such as chicken embryo cells, VERO cells, CV-1 cells, LLC-MK-2 cells, MDCK cells, MDBK cells, WI-38 cells or MRC-5 cells.

The biologically active nucleic acid disintegrated according to a preferred embodiment of the method of the invention is derived from the cells and/or the virus.

According to the present invention, vaccines useful for the inoculation of mammalian hosts, including both animals and humans, against viral or bacterial infections are provided. The vaccines are prepared by disintegration of biologically active nucleic acids of a microorganism, such as a live virus or a prokaryotic cell, without negatively affecting the biological integrity and activity, such as antigenicity, immunogenicity or protectively of said microorganism. The disintegration process is performed in a suitable medium optionally containing a photodynamic substance in a concentration sufficient to disintegrate essentially all biologically active nucleic acid upon exposure to laser beam. By using a photodynamic substance in a concentration which allows binding of the substance to the nucleic acid and exposure to laser beam to disintegrate the biologically activity of the nucleic acid, the degradation of the antigenic and immunogenic characteristics of proteins is avoided. Optionally, prior to the exposure of the biological material to the laser beam, a quencher and/or scavenger and/or stabilizer may be added.

The present invention is suitable for producing vaccines to a wide variety of viruses, including human viruses and animal viruses. The method is suitable for inactivating double-stranded DNA viruses, single-stranded DNA viruses, double-stranded RNA viruses and single-stranded RNA viruses, including both enveloped and non-enveloped viruses, such as selected from the group of adenovirus, herpes virus, papovavirus, poxvirus, parvovirus, reovirus, retrovirus, myxovirus, paramyxovirus, picornavirus, Toga virus, flavivirus, orthomyxovirus or rhabdovirus. In particular, the virus is an influenza virus, herpes simplex virus, HIV, HBV, HAV, HCV, HSV, TBEV or CMV.

The present invention also is suitable for the production of virus vaccines, wherein the virus to be inactivated is an attenuated virus. This is especially advantageous in such case, where the original active virus is highly virulent, e.g. HIV or HCV, so that the manufacture process by itself would cause safety problems for the laboratory personal by working with high titer virus preparations. By using an attenuated virus strain for the vaccine production process the risk is less than using the virulent strain. In addition, although by the present method a completely inactivated, non-infectious virus having all its biologically active nucleic acids disintegrated is obtained, the use of an attenuated virus for vaccine preparation instead of the virulent form would maximize the safety of such a vaccine.

In preparing the subject vaccines, sufficient amounts of the virus to be inactivated may be obtained e.g. by concentrating virus from highly contaminated plasma. Highly contaminated plasma can be conventionally fractionated by use of ethanol/PEG precipitation, Sephadex adsorption and other conventional purification steps to make highly concentrated preparations of these viruses which then can be inactivated by treatment with a photodynamic substance and/or laser beam. Viruses may also be concentrated by the use of nanofiltration techniques, wherein optionally small viruses such as parvovirus can be complexed with specific antibodies to create an immuncomplex which can be retained by nanofiltration. This technique is preferably used for viruses which cannot be cultivated in cell cultures, such as HCV, HBV or parvovirus. The subject vaccines may also be obtained by growing seed virus in a suitable vertebrate cell culture. Seed virus may be obtained by direct isolation from an infected host or from a source such as a collection of microorganisms. Suitable cell cultures include primary or secondary cultures derived from tissues or established cell lines such as CEC, Vero cells, monkey kidney cells, BHK cells, CV-1 cells, LLC-MK-2 cells, MDCK cells, MDBK cells, LTMK cells, WI-38 cells, MRC-5 cells or other cells permissive for the desired virus and which may be grown as monolayers or suspension culture. The cell culture is either obtained by conventional methods such as by growing cells in serum-containing medium, or more preferably they are grown under serum or protein-free conditions from the original ampoule to a large scale cellular biomass. Unexpectedly, it has been found that when treatment with photoactive substance and/or laser beam is performed under serum or protein free conditions the nucleic acid disintegration process is highly efficient and biological integrity and activity, such as the immunogenic and antigenic characteristics of the proteins are substantially maintained.

Therefore according to a substantial aspect of the present invention virus infection is preferably performed under serum or protein-free conditions. This can be done by growing the cell culture in serum or protein free medium for several generations prior to infection or by replacing serum-containing growth medium with serum or protein free medium prior to infection. Cells are infected with the virus under standard conditions with a multiplicity of infection (m.o.i) preferably between 0.001 and 0.1 $TCID_{50}$, in particular at about 0.01. Cell growth, infection and virus production are monitored periodically. The monitoring can be by automated or other means and results of the monitoring can be used to control the production process. By infecting and incubating the cellular biomass with the virus, a cell culture is obtained comprising a virus-containing supernatant and/or a cellular biomass comprising virus and virus antigen. Depending on the nature of the virus used, the virus particles produced are either found in the supernatant of the cell culture and/or are associated with the cellular biomass.

Examples of lytic viruses include influenza virus and vaccinia virus. The virus is produced and released in the cell culture medium to produce a virus-containing medium. The virus-containing medium may be removed from the cell culture and either exposed directly to laser beam or optionally treated with a selected concentration of a photodynamic substance prior to exposure to laser beam. The virus-containing biological material can be removed in portions or completely in a continuous process or batchwise manner from the cell culture vessel and transferred to a second container to which the photoactive substance is added. The photodynamic substance may be added to the viral suspension in a single addition or in multiple additions, the virus being exposed to a laser beam between the additions, or may be added thereto continuously during the entire treatment period, or a portion thereof. Usually the number of addition will be 1. According to the present invention this can be done by recycling the photodynamic substance and the laser beam treated medium in a continuous process. The virus-containing medium is transferred from the culture vessel to a container, where the photodynamic substance is added in a selected concentration and said mixture is pumped through a system with a window for exposure to laser beam for a time sufficient to disintegrate essentially all biologically active nucleic acid.

According to the method of the invention during all steps of the virus inactivation process one or more quencher(s) and/or scavengers and/or stabilizer(s) may be added alone or in any suitable combination. The inactivated virus is further subjected to purification or the virus-containing material is pumped back directly to the second container or pumped in the reverse direction through the window for a second cycle of exposure to laser beam, where a second portion of photodynamic substance and/or quencher and/or scavenger and/or stailizer might be added or not, and subjected to a second cycle of laser beam. This process can be repeated for several cycles, preferably 5 to 50 cycles, in particular 10 to 30 cycles.

During laser beam irradiation, the medium may be maintained still, stirred or circulated and may be either continuously exposed or be subjected to alternating periods of exposure and non-exposure. The circulation may be in closed loop system or in a single system ensuring that all the samples have been exposed to light.

During infection and propagation not all virus particles produced by the cell are released in the supernatant. Rather, these particles are still associated with the cells of the cellular biomass. Therefore, the cell culture contains virus particles in the supernatant and complete virus particles as well as virus proteins associated with the cellular biomass. To obtain an increased virus yield, the virus particles from the supernatant are harvested and the virus and/or virus antigen associated with the cellular biomass is isolated. The virus found in the cells of the cellular biomass is released from the cells by lysis. The cells can be lysed by conventional methods, such as treating the cells with a detergent, treating with heat, sonication, French-press or other cell lysing methods. The viruses released from the cells are harvested by e.g. centrifugation and resuspended in a buffer. Viral antigens still associated with the cellular biomass or with cell fragments can be extracted from the cells or cell fragments by chemical or mechanical methods known in the art. These methods include ultrasonication or treatment with an appropriate detergent to release the virus antigen from the cell or cell fragments, especially from the membrane. The nucleic acids in that suspension either derived from the cells or the virus are disintegrated by exposure to laser beam or by treating the solution with a preselected concentration of a photodynamic substance and subsequent exposure to laser beam. The virus antigen, including viruses, isolated from the cellular biomass, then, can be further subjected to a purification step including separation on a sucrose-gradient, adsorption to a chromatography column, washing and eluting the purified virus or virus antigen. The chromatography column used is selected from ion-exchange chromatography, affinity-chromatography or size filtration chromatography.

The virus-containing medium also can be replaced by an inorganic buffer by centrifugation and suspension in an aqueous buffered medium. The inorganic buffer is preferably a phosphate-buffer or Tris/HCl. The amount of virus yield in the suspension will generally be about $10^6$ to $10^9$ pfu/ml, preferably about $10^7$ to $5\times10^8$ pfu/ml.

Furthermore, the invention comprises the step of preparing a vaccine with the inactivated virus/virus antigen.

Although disintegration of nucleic acid in a microorganism-containing biological material according to the present invention will normally be carried out in an inactivation or disintegration solution, in some cases it my be desireble to introduce the photodynamic substance directly to the cell culture medium in which the virus is grown. Under such conditions, the cell culture may be grown several generations in serum or protein free medium in the presence of a photodynamic substance, preferably prior to infection, in the dark and under optimal growth conditions. After virus infection and virus propagation the nucleic acid disintegration is carried out by removing the live virus-containing medium treated with photodynamic substance or not from the cell culture and exposure of the viral particles to laser beam of a selected wavelength in the inactivation medium which may or may not contain additional photodynamic substance and/or quencher and/or scavenger and/or stabilizer.

With the method of the present invention the possibility to employ less rigorous inactivation conditions is of great benefit in preserving the antigenicity, immunogenicity and protectivity of the virus during disintegration of viral nucleic acid. It has been unexpectedly found that under the present conditions, when virus is treated with a photodynamic substance and irradiated with laser beam, particular viruses, especially non-lipid viruses, having rigid capsids, can be inactivated with complete loss of infectivity. In some cases it might be desirable to add an organic solvent to increase the permeability of the outer coat or membrane of the virus. Such increase in permeability facilitates penetration by the photodynamic substance and enhances the disintegration of the viral nucleic acid in the inner core of the virus. The photodynamic substance and the organic solvent may also be added to the cell culture medium in which the virus is grown.

It may be desirable to remove the expended photodynamic substance and/or its degradation products from the mixture. This can be accomplished by one or more standard laboratory procedures such as dialysis across an appropriately sized membrane or an hollow fiber system after completion of the laser beam exposure. Alternatively, one could use affinity or gel filtration chromatography methods for one or more of the low molecular weight materials to be removed.

It has been found that such conditions allow the preparation of inactivated, enveloped or non-enveloped viruses, wherein essentially all biologically active nucleic acid is disintegrated, without negatively affecting the biological integrity and activity, such as the antigenic and immunogenic properties, of the inactivated virus. Thus, viruses which have been resistant to inactivation and disintegration of the nucleic acid or could only inefficiently be inactivated, can be completely inactivated without the loss of the desired biological activity. Viruses which have previously been successfully inactivated may now be inactivated under conditions which better preserve their antigenic characteristics, making them more efficient immunogenic substances for use in vaccines.

The present invention also provides a method for virus propagation and virus inactivation in a closed one step system, which will ensure that during the manufacture process no workers will come into contact with a non-inactivated virus.

The inactivated virus may be formulated in a variety of ways for the use as a vaccine. The concentration of the virus will generally be from $10^6$ to $10^9$ pfu/ml with a total dosage of at least $10^5$ pfu/ml, usually at least $10^6$ pfu/ml, preferably at least $10^7$ pfu/ml. Suitable vaccines may be prepared by combining the inactivated viruses with a physiologically acceptable carrier, typically an adjuvant, in an appropriate amount to elicit an immune response e.g. the production of serum neutralizing antibodies, upon subsequent inoculation of the host. It may be in an inert physiologically acceptable medium, such as ionized water, phosphate-buffered saline, or saline, or may be administered in combination with a physiologically acceptable immunologic adjuvant, including but not limited to mineral oil, Freund's Adjuvant, vegetable oils, mineral salts and immunopotentiators. The vaccine may be administered subcutaneously, intramuscularly, intraperitioneally, orally or nasally. Usually, a specific dosage at a specific site will range from about 0.1 to 1.0 ml, where the total dosage will range of about 1.0 ml to 10 ml. The number of injections and their temporal spacing may be highly variable, but usually 1 to 3 injections at 1, 4 and 24 weeks intervals are effective.

According to another aspect of the invention the method further provides for the treatment of virus infection and/or the prevention of virus infection by administering to an animal or a human a vaccine as described above.

The reduction or loss of infectivity and complete inactivation of viruses is conventionally determined by blind passage of samples using a biological assay such as an enzyme assay (e.g. reduction in reverse transcriptase) or determination of viral titer, CPE, $TCID_{50}$, pfu/ml or in an animal model. A more sensitive method has been described by Hanson et al. (1990, J. Clin. Microbiol. 28: 2030–2034). Indeed, it has been found that this approach of measuring viral inactivation typically cannot distinguish between the situation where inactivation of the virus is complete from the situation where inactivation is not complete and residual biologically active viral nucleic acid could still be infectious in vivo. For the preparation of an inactivated virus vaccine of e.g. HIV it would be highly desirable to ensure that the infectivity has been lost and all active nucleic acid of the virus has been completely disintegrated. This requires the use of an improved inactivation method and the quantification of the residual biologically active nucleic acid with a highly sensitive, accurate and reproducible method.

Bachmann et al. (1995, J. Med. Virol. 47:172–178) disclosed the use of PCR inhibition assay to estimate the amount of viral RNA after inactivation with methylene blue and light. They did not detect viral nucleic acid after 25 amplification cycles, whereas specific amplification products were found when the RNA was amplified for 30 cycles. Therefore, the nucleic acid quantification assay did not allow for an accurate determination of the inactivation process and also did not show any evidence that the inactivation of the nucleic acid by this method was complete. One therefore needs a comprehensive and quantitative method to determine the inactivation efficiency.

The present invention involves measuring the inhibition of template-dependent enzymatic synthesis of nucleic acid following the exposure of a biologically active material to laser beam, optionally after the addition of a photoactive substance that binds to nucleic acid and after exposure to laser beam, to disintegrate the active nucleic acid. Thus, when the nucleic acid is disintegrated by the method of the present invention, attempts to amplify nucleic acid would result in no amplification product. The reagents for the amplification of e.g. the viral nucleic acid are typically specific for the virus and/or the cellular nucleic acid of the cell culture either used for virus propagation or for production of a genetically engineered product.

The present invention also provides a method of determining the efficiency of a nucleic acid disintegration technique, comprising the measurement of the ability of the disintegration process to inhibit replication of viral nucleic acid as measured by a nucleic acid amplification assay. The amplification process is the highly sensitive polymerase chain reaction (PCR), such as described above. The efficiency of the disintegration process can be determined by the failure to detect amplified products of the polymerase chain reaction. The efficacy of the PCR process can be checked by the use of at least two different internal standards which differ from the sequence to be amplified in at least one marker.

The disintegration of biologically active viral nucleic acid in the disintegration mixture is determined by the steps of providing virus-containing biological material that has been treated to disintegrate biologically active nucleic acid, treating a sample of the mixture so that the viral nucleic acid is released from the virus particles, preparing a suspension such that the nucleic acid of the virus is amplifiable and adding to that mixture a set of primers and at least one internal standard that differs from the nucleic acid to be amplified in at least one marker and performing an amplification reaction sufficient to provide amplification products. The nucleic acid to be determined and amplified in a nucleic acid disintegrated virus suspension derived from a cell culture system is the nucleic acid derived from the virus and the nucleic acid derived from the cell culture.

The present invention provides a method for production of a safe inactivated, non-infectious vaccine which eliminates the risks of transmitting biologically active nucleic acid to the vaccinated host. The present invention also provides for a method for production of safe, non-infectious biological material.

According to the present invention, the nucleic acid content of active nucleic acid in a biological material is determined and quantified after the disintegration step by a nucleic acid amplification method, preferably PCR. The parameter of the disintegration capacity is the complete loss of detection of active nucleic acid determined by PCR.

By this mode of procedure, the disintegration of the nucleic acid can be checked. Preferably, the method is carried out such that after the treatment with a photoactive agent and laser light, the content of the nucleic acid to be detected is less than 100 pg, preferably less than 10 pg, particularly preferred less than 1 pg per dose or fewer than 500 copies/ml, preferably fewer than 300 copies/ml or 1 to 500 copies/ml at the most. The nucleic acid content preferably is below the detection limit of a nucleic acid quantitation method of the prior art considered to be very sensitive.

In case after disintegration nucleic acid template activity is still measured by PCR, the disintegration process will be adapted to conditions that allow complete reduction of nucleic acid template activity.

When the present method of disintegration of biologically active nucleic acid is used to inactivate e.g. pathogens either used for the preparation of vaccines or to obtain noninfectious biological material it is essential that disintegration of biologically active nucleic acid is complete.

In connection with the present invention it has been found that with the method according to the invention a virus inactivation of at least 7 log steps is possible, measured both by determining the virus titer and the copy number of the viral or genomic nucleic acid, the disintegration occurring irrespective of the type of nucleic acid. For inactivation of non-enveloped viruses hitherto known to be photoresistant, possibly an increase in the concentration of the photoactive substance is necessary, the light energy used, however, remaining unchanged low, in a range of below 0.1 J/cm$^2$.

The disintegration of the nucleic acid in a biologically active material according to the present invention is measured by nucleic acid amplification. This is performed by a sensitive, quantitative, accurate and reproducible method to determine nucleic acid activity that indicates the efficacy of the disintegration process. The method, therefore is used as a quality control assay to verify adequate treatment of a biological material, with laser beam or photodynamic substance/laser beam.

If the method is used for the preparation of a vaccine the immunogenicity after laser beam or photodynamic substance/laser beam disintegration is usually assessed by immunization and protection studies in laboratory animals such as mice or rabbits, determination of the binding antibody titer, and neutralization assays. To ensure that the inactivation method has not altered the integrity and activity, such as antigenic and immunogenic properties, of the biological, a more sensitive method for the determination of the antigenicity has been also used. The maintenance of biological integrity and activity, such as antigenicity and— immunogenicity of biological products treated according to the method of the invention is tested by epitope mapping and potency test or by activity test.

In another aspect of the invention there is provided a method for disintegration of a biologically active nucleic acid in a biological material comprising a genetically engineered proteinaceous product, wherein the biologically active material is exposed to laser beam to disintegrate essentially all biologically active nucleic acid in the material, while the biological integrity and activity of the genetically engineered proteinaceous product is maintained. In one preferred embodiment of the method prior to exposure to laser beam a photodynamic substance is added to the biologically active material. The biological material comprising a genetically engineered proteinaceous product may be derived from genetically modified cells transfected with a viral vector comprising a foreign nucleic acid to be expressed, a genetically modified cell having a foreign nucleic acid stable inserted in the genome or a hybridoma cell line producing a monoclonal antibody. Suitable genetically modified cells are vertebrate cells such as those selected from VERO cells, CHO cells, BHK cells, chicken embryo cells, MDCK cells, CV-1 cells, LLC-MK2 cells, MDBK cells, WI-38 cells, MRC-5 cells, SK-Hep cells or another continous cell line, such as a tumor cell line or a hybridoma cell line. The genetically engineered proteinaceous product is a protein derived from a virus, a bacterium, a blood factor, a cytokine, a chemokine, a hormone or a monoclonal antibody.

The genetic modification of the cells can be performed by transfecting the cells with a viral vector comprising a foreign nucleic acid to be expressed under the control of a transcriptional and a translational element. The viral vector can be an adenovirus vector or a poxvirus vector, preferably a vaccinia virus vector. Suitable genetically modified vertebrate cells are also cells that have a foreign nucleic acid inserted in their genome. The foreign nucleic acid inserted into the viral vector or stably inserted in the genome of cells can encode a recombinant protein, such as viral proteins, preferably antigens, bacterial proteins and blood factors. Preferred viral antigens are those of HIV, such as gp160 or gp120, those of HBV, such as HBsAg, preS2 or pres1, those of HCV, those of parvovirus, those of HAV, those of TBEV, such as prM/M or E, those of influenza virus, such as HA or NA. Preferred bacterial antigens are those selected from Borrelia, pseudomonas and Haemophilus influenzae. Preferred blood factors include Factor II, Factor V, Factor VII, Factor VIII, Factor IX, Factor X, Factor XI, Factor XIII, Protein C, Protein S, von Willebrand Factor and antithrombin III. Other recombinant proteins include proteins of the group of cytokines, chemokines or hormones.

According to one embodiment of the method of the invention the recombinant protein is produced and released in the culture medium. The proteinaceous product is concentrated and resuspended in a appropiate buffer solution, optionally treated with a photodynamic substance, and exposed to laser beam. Preferably, the photodynamic substance is directly added to the culture medium without any prior manipulation. The culture medium containing the genetically engineered product and the photodynamic substance is then exposed to laser beam. The process can be performed in a similar manner as described for the preparation of inactivated virus.

In case the protein produced by genetically modified cells is not released in the supernatant but still is associated with the cells, the product can be isolated from the cells by a conventional method, such as concentration of the cells, extraction and resuspension in an appropiate buffer. The buffer solution comprising the proteinaceous product is then further exposed to laser beam, optionally after addition of a photoactive substance, as described above.

In accordance with another aspect of the invention, there is provided a method for the disintegration of a biologically active nucleic acid in a microorganism-containing biological material, wherein a microorganism-containing biologically active material is exposed to laser beam to disintegrate essentially all biologically active nucleic acid in the biological material, while the biological integrity and activity, such as antigenicity, immunogenicity and protectivity, of the microorganism in the biological material is maintained. Preferably, the microorganism is a bacterium.

In accordance with another aspect of the invention, there is provided a method for the production of an inactivated microbiological vaccine, wherein a biologically active material comprising a microbiological is exposed to laser beam to disintegrate essentially all biologically active nucleic acid in the material, while the biological integrity and activity, such as antigenicity and immunogenicity, of the microbiological in the biological material is maintained, subjecting the inactivated microorganism to further purification and formulate the inactivated and purified microorganism with a physiologically acceptable carrier. In one preferred embodiment of the method a photodynamic substance and/or a quencher and/or scavenger and/or stabilizer is added to the biological material prior to exposure to a laser beam. Bacterial vaccines can be prepared by inactivation of bacterial pathogens in the culture, medium or buffer according to the method of the invention, wherein said bacteria are selected from the group of pneumococci, streptococci, staphylococci, neisseriae, enteric bacilli, pseudomonas, haemophilus, bortedella, mycobacteria or spirochaetes or a viral pathogen, such as a lipid or non-lipid virus.

In accordance with another aspect of the invention there is provided a biologically active material having been exposed to laser beam, wherein the biological material has disintegrated biologically active nucleic acid, while its biological integrity and activity, such as antigenic, immunogenic and protective properties, have bee maintained.

In accordance with another aspect of the invention there is provided a biologically active material having been treated with a photodynamic substance and exposed to laser beam, wherein the biological material has disintegrated biologically active nucleic acid, while its biological integrity and activity, such as antigenic, immunogenic and protective properties, have been maintained. According to the invention the biological material provided is a blood factor, a plasma protein derived from fractionation of blood or blood plasma, a virus or virus antigen, a viral or bacterial vaccine or a genetically engineered proteinaceous product, such as a recombinant protein or a monoclonal antibody.

In accordance with another aspect of the invention there is provided a pharmaceutical preparation comprising a biological material as described above and a pharmaceutically acceptable carrier. The pharmaceutical preparation of the present invention can be used for the treatment of a mammal.

The invention will now be explained in more detail by the following examples and the drawing FIGURE to which, however, it shall not be restricted.

FIG. 1 shows a system for laser beam activation of a photodynamic substance which has been added to a biological material.

A photodynamic systance is added into a container (A) containing the biological material. The latter is pumped through a system comprising a window (B) for exposure to a laser beam into a second container (C). It may be pumped back in reverse diretion or recirculated so as to allow the sample to be subjected to several cycles of laser beam treatment.

EXAMPLES

Example 1

Inactivation of HIV-1, TBEV, Influenza Virus, HSV-1 and Polio Virus by Methylene Blue/Laser Beam Treatment (presently considered by applicant to be the best mode of carrying out the invention)

A schematic description of the procedure is shown in FIG. 1. A system is used in which the biological material is passed through a little tube or a cuvette having a glass window, and the glass window is irradiated with the laser beam. The energy density acting on the biological material determined by the radiation intensity of the laser used×the dwell time of the liquid in the region of the laser radiation. There, the radiation intensity of the laser is the laser output per laser radiation area. The dwell time within the beam depends on the geometry of the glass window and on the flow rate.

One hundred ml of virus stock solution are maintained in a flask which is held at 4° C. with stirring. A methylene blue stock solution with a concentration of 10 mM is added to give a final concentration of 2 μM. After thorough stirring the material is pumped through a stainless steel tube with a glass window through which it is irradiated by a laser beam from a He-Ne-Laser at a wavelength of 633 nm with a working intensity of 10 mW. With a square diameter of the glass window of 2×2 mm and a flow rate of 4 ml/min, there results a flow rate through the irradiated region and thus a dwell time of 0.06 sec/mm. Departing from a laser output of 10 mW, the laser intensity thus is 0.6 mWs/mm$^2$ or 0.06 J/cm$^2$ per cycle. The material was recirculated for 0 to 30 cycles of irradiation and samples were drawn for virus titration after the number of cycles as described above. Controls with methylene blue were subjected to 30 cycles under identical conditions but without irradiation. Virus titres were determined before and after methylene blue/laser treatment and are summarized in Table 1.

TABLE 1

Inactivation of HIV-1, TBEV, Influenza, HSV-1 and Polio Virus by Methylene Blue/Laser Beam Treatment

| Treatment | HIV-1 | HSV-1 | TBEV | Influenza | Polio |
|---|---|---|---|---|---|
| None | $10^{7.0}$ | $10^{8.4}$ | $10^{7.3}$ | $10^{8.2}$ | $10^{8.9}$ |
| 1 Cycle | $10^{6.5}$ | $10^{7.5}$ | $10^{6.2}$ | $10^{7.7}$ | $10^{8.7}$ |
| 2 Cycles | $10^{6.1}$ | $10^{6.0}$ | $10^{5.7}$ | $10^{5.5}$ | $10^{8.6}$ |
| 5 Cycles | $10^{1.9}$ | $10^{2.0}$ | $10^{2.9}$ | $10^{1.7}$ | $10^{8.9}$ |
| 10 Cycles | $<10^{0.2}$ | $<10^{0.2}$ | $<10^{0}$ | $<10^{0.2}$ | $10^{8.8}$ |
| 20 Cycles | $<10^{0.2}$ | $<10^{0.2}$ | $<10^{0}$ | $<10^{0.2}$ | $10^{6.4}$ |
| 30 Cycles | $<10^{0.2}$ | $<10^{0.2}$ | $<10^{0}$ | $<10^{0.2}$ | $10^{4.4}$ |
| 30 Cycles with laser beam/without MB | $10^{6.4}$ | $10^{7.9}$ | $10^{7.0}$ | $10^{7.1}$ | $10^{8.2}$ |
| 30 Cycles without laser beam/+MB | $10^{6.9}$ | $10^{8.1}$ | $10^{7.1}$ | $10^{7.6}$ | $10^{8.1}$ |

Example 2

Inactivation of Polio Virus by Methylene Blue/Laser Beam Treatment with Increased Concentration of Methylene Blue A methylene blue stock solution was added to one hundred ml of a Polio virus stock solution to give end concentrations of 1, 3, 10 and 30 μM, respectively. Each sample was irradiated as described in Example 1 for 30 cycles, with 0.06 J/cm$^2$ each. Virus titres were determined after irradiation at each methylene blue concentration. It could be demonstrated that non-enveloped polio virus is inactivated with more than 8 log steps.

TABLE 2

Inactivation of Polio Virus by Methylene Blue/Laser Beam Treatment

| MB Conc. (μM) | Virus Titre |
|---|---|
| 1 | $10^{8.9}$ |
| 3 | $10^{6.2}$ |
| 10 | $10^{2.7}$ |
| 30 | $<10^{0.2}$ |

Example 3

Comparison of the Antigenicity of Methylene Blue/Laser Beam and Formalin Inactivated Vaccine Preparations Sucrose gradient purified whole virus preparations of HIV-1, Influenza A/FPV/Rostock/34, a Tick-Borne Encephalitis Virus and a purified viral glycoprotein subunit preparation from HSV-1 infected Vero cells were subjected to 30 cycles of methylene blue (2 μM)/laser beam (10 mW) treatment. Identical preparations were inactivated by formalin treatment (0.05% end concentration, 30 h at 37° C.). Following safety testing as described in Example 1 to ensure that no infectious virus was present, the antigenicity of all preparations was determined.

The antigenicity of the HIV-1 preparations was determined by use of commercial antigen capture ELISA. The methylene blue/laser beam inactivated preparations were serially two fold diluted before adding 100 μl of each dilution to a well precoated with purified anti-HIV-1 IgG. The plates were then extensively washed and 100 μl of human anti-HIV-1 antibody covalently linked to horseradish peroxidase were added and incubated at room temperature for 90 minutes. Two hundred microlitres of activated substrate (0-phenylenediamine) were then added and incubated until the reaction was stopped by addition of 50 μl 8M sulphuric acid and the absorbance was read at 490 nm. The antigen titre was determined as the reciprocal of the highest dilution which gave a positive reaction.

The TBEV antigenicity was also determined by antigen capture ELISA using a purified guinea-pig anti-TBEV IgG as capture antibody. The inactivated preparations were serially two fold diluted and 100 μl of each dilution added and incubated at 37° C. for 90 minutes. Following washing, 100 μl of rabbit anti-TBEV serum were added and following incubation for 60 minutes 100 μl of peroxidase linked anti-rabbit IgG were added. Two hundred microlitres of activated substrate (O-phenylenediamine hydrochloride) were then added and incubated in the dark until the reaction was stopped by addition of 50 μl 8M sulphuric acid and the absorbance was read at 490 nm. In addition, a highly purified TBEV antigen preparation was used as a standard in the ELISA which allowed direct calculation of the amount of reactive TBEV antigen.

HSV antigen reactivity was also measured using a modified commercial ELISA kit. The antigen samples were serially two fold diluted and 100 μl of each dilution were added to plates precoated with a purified rabbit anti-HSV-1 IgG. After incubation and washing a horseradish peroxidase conjugated anti-HSV-1 antibody was added. This was incubated at 37° C. for 1 hour and after washing 100 μl of activated substrate (0-phenylenediamine hydrochloride) were added and incubated in the dark for 10 minutes. The reaction was stopped by the addition of 50 μl 5M sulphuric acid and the absorbance was read at 490 nm. The antigen titre was determined following construction of a standard curve using a highly purified HSV-1 antigen standard, whose reactivity was determined in the ELISA system. The antigenicity of influenza was measured by the hemagglutination assay i.e. agglutination of virus with erythrocytes. This was carried out as described by Hirst "The Agglutination of Red Cells by Allantoic Fluid of Chicken Embryos infected with Influenza virus", Science 94: 22–23 (1941). The results are summarized in Table 3.

TABLE 3

Comparison of the Antigenicity of Methylene
Blue/Laser Beam and Formalin Inactivated Vaccines

|  | Formalin | Methylene Blue |  |
| --- | --- | --- | --- |
| HIV | 1:2160 | 1:5120 | Antigen ELISA Titre |
| Influenza | 10 | 11 | HA Titre HAU |
| TBEV | 40.7 µg/ml | 39.4 µg/ml | Antigen Conc. |
| HSV | 9001 | 12,370 | ELISA Units/ml |

Example 4

Immunization of Mice with Formalin Inactivated and Methylene Blue/Laser Beam Inactivated HIV-1

A sucrose gradient purified HIV-1 preparation with a titre of approx. $10^7$ $TCID_{50}$/ml was inactivated with a formalin end-concentration of 0.05% for 30 h at 37° C. Following his treatment formalin was removed by dialysis. The same HIV-1 preparation was subjected to 10, 20 and 30 cycles of laser beam treatment as described previously following addition of methylene blue to give an end concentration of 2 µM. Methylene blue was then removed by passage over a G-25 Sephadex column. The protein content of all preparations was determined and adjusted. Groups of ten mice were immunized with 10 µg of each preparation adjuvanted with $Al(OH)_3$ and boostered four weeks later with the same antigen dose. The mice were sacrificied for serum preparation two weeks after the second immunization and following pooling of sera from animals in each group the HIV-1 specific antibody titre was determined using a commercial whole virus ELISA kit. Briefly, sera were serially two fold diluted and 100 µl of each dilution were added to the precoated plates and incubated at 37° C. for 1 hour. After extensive washing each well was filled with 100 µl of horseradish peroxidase conjugated anti-mouse IgG and incubated at 37° C. for 1 hour. After washing, 200 µl of activated substrate (0-phenylene-diamine hydrochloride) were added to each well and incubated at room temperature in the dark for 10 minutes. The reaction was stopped by the addition of 50 µl 5M sulphuric acid and the absorbance was read at 490 nm. The antibody titre was determined as the reciprocal of the highest dilution which gave a positive reaction. Results are summarized in Table 4.

TABLE 4

Comparison of the Immunogenicity of Laser
Beam/Methylene Blue and Formalin Inactivated HIV-1

| Inactivation Method | Mean HIV-1 ELISA Titre |
| --- | --- |
| 10 Cycles Laser/MB | 38,000 |
| 20 Cycles Laser/MB | 40,000 |
| 30 Cycles Laser/MB | 36,000 |
| Formalin | 36,000 |

Example 5

Comparison of the Disintegration of HIV-1 Nucleic Acid by Methylene Blue/Laser Beam and Formalin Treatment An HIV-1 virus preparation was inactivated by treatment with 0.05% formalin end concentration for 30 h at 37° C. or by treatment with laser beam as described in Example 4 for 10, 20 or 30 cycles following addition of methylene blue to give an end concentration of 2 µM. The virus titre was calculated using a standard $TCID_{50}$ methodology (Reed et al., 1938, Amer.J.Hyg. 27:493–497). RNA copy number was determined according to the following procedure:

500 µl of the inactivated virus preparation were centrifuged in an ultra-centrifuge at 70,000 rpm for 20 min. The pellet was taken up in 1 ml of guanidium isothiocyanate solution (RNAzol® of Biotec), and 5 µl of 1 mg/ml t-RNA from yeast and a certain amount, e.g. 20 µl, of standard RNA were added. A pre-determined number, e.g. 400 and 1200, copies of the minus- and plus-RNA standards were added and vortexed. The solution was heated for 10 min at 70° C., then ¹/₁₀ volume of chloroform was added and incubated on ice for 10 min. Thereupon it was centrifuged in a table-top centrifuge for 5 min, the supernatant was transferred into new vials. 500 µl of isopropanol were added and adjusted to −80° C. for 15 min. Subsequently, it was centrifuged for 10 min, washed twice with 70% ethanol, and the pellet was taken up in 50 µl of water. 5 µl were used for the RT-PCR.

The standard plasmids pgag−15 and pgag+12 used were derived from the plasmid pgag1 which consists of the known pBS/SK plasmid (of Stratagene) and an insert in the multiple cloning site of this plasmid, which insert contains the bp 1417 to 2008 of the HIV-1 from Ratner et al. (1985, Nature 313: 277–284). In pgag−15, the bp 1593 to 1607 were deleted, in pgag+12 an insert of 12 bp was inserted at site 1593.

In this quantitation primers were used which bind in the cDNA sequences of HIV-1 and which yield a product of 115(wt) bp by means of RT-PCR of wild-type RNA, namely:

SK38 (SEQ ID NO:1): ATAATCCACCTATCCCAG-TAGGAGAAAT HIV-1 1551–1578 and

SK39 (SEQ ID NO:2): TTTGGTCCTTGTCTTATGTC-CAGAATGC HIV-1 1665–1638 (Numbering according to Ratner et al.). The length of the RT-PCR products of the standard and of the wild-type DNA thus were 127 (pgag+12) and 100 (pgag−15). The primers were produced by using the phosphoamidite chemistry on a DNA synthesizer (Applied Biosystems 394 DNA Synthesizer).

The RT-PCR set-up contained, in a known manner, one aliquot of the extracted nucleic acid, RT buffer of Perkin-Elmer, $MgCl_2$, dNTPs, the RT primer and rT.th.polymerase (Perkin-Elmer, 2.5 U/µl) and water. The RT-PCR was carried out according to the instructions of the producers of buffer and enzyme and according to the common working instructions (Mullis et al., Methods in Enzymology 155 (1987), 335–350) respectively, in a PCR apparatus (GeneAmp PCR System 9600 of Perkin-Elmer).

For determining and quantitating the PCR products, 0.5 to 1.0 µl of the PCR solution were taken and analysed in a Genescanner 373A instrument of Applied Biosystems according to the instructions of the producer.

The RNA copy number of HIV virus preparations prior to and after methylene blue/laser beam treatment were determined and the results are summarized in Table 5.

TABLE 5

Comparison of the Disintegration of HIV-1
Nucleic Acid by Methylene Blue/Laser Beam and Formalin
Treatment by Determining the Virus Titre and RNA Copy
Number

| Treatment | Virus Titre ($TCID_{50}$/ml) | HIV-1 RNA (Copy Number/ml) |
| --- | --- | --- |
| Virus Stock Solution | $10^{7.6}$ | $10^{10}$ |
| Virus Stock Solution with MB | $10^{7.1}$ | $10^{9.8}$ |

TABLE 5-continued

Comparison of the Disintegration of HIV-1
Nucleic Acid by Methylene Blue/Laser Beam and Formalin
Treatment by Determining the Virus Titre and RNA Copy
Number

| Treatment | Virus Titre (TCID$_{50}$/ml) | HIV-1 RNA (Copy Number/ml) |
|---|---|---|
| 10 × Cycles Laser with MB | <10$^{0.3}$ | <10$^{2.6}$ |
| 20 × Cycles Laser with MB | <10$^{0.3}$ | <10$^{2.6}$ |
| 30 × Cycles Laser with MB | <10$^{0.3}$ | <10$^{2.6}$ |
| Formaldehyde | <10$^{0.3}$ | <10$^{8.3}$ |

Example 6

Disintegration of HSV-DNA and CEC DNA by Methylene Blue/Laser Beam Treatment

An HSV-1 glycoprotein subunit vaccine was prepared from HSV-1 infected chicken embryo cells by detergent extraction, sucrose gradient purification followed by lentil-lectin chromatography. This preparation was then subjected to formalin inactivation (30 h, 0.05% formalin end-concentration at 37°) or to methylene blue/laser beam treatment with 30 cycles with a methylene blue end concentration of 2 μM. Chicken embryo cell and HSV-1 DNA in the methylene blue/laser and formalin treated sample was determined prior to and after both treatments.

For HSV DNA quantitation primers were used which bind in the genome of HSV and give a product of 114 bp by PCR of wild-type DNA, namely gDR1/B (SEQ ID NO:3): AAC TAC CCC GAT CAT CAG and gDR2/B (SEQ ID NO:4): AGG CCC ACT TAG ACG ACA.

The standard plasmid pHerp-9 was derived from the plasmid pHerp which consists of the known pCRII plasmid (of In Vitrogen) and an insert of bp 128364 to 138784 of the HSV genome (McGeoch D. J. et al., EMBL GenBank ID HE1CG1). 9 bp were deleted in pHerp-9. The plasmids pHerp and pHerp-9 were purified, the concentration was determined by spectroscopic measurement at 260 nm, it was linearised with a restriction enzyme and diluted in a TE buffer (10 mM Tris/HCl, 1 mM EDTA, pH 8).

This DNA preparation serves as a standard for the PCR. The lenghts of the PCR products of standard and wild-type thus were 105. (pHerp-9) and 114 bp (pHerp).

The chromosomal chicken DNA was quantitated by using the primer pair

CR1 (SEQ ID NO:5): ATGAGGCACTGGAACAGGT-TGCCC and

CR1A (SEQ ID NO:6): AGGGCCACATCCAGCCTGG.

These primers are specific for repetitive avian sequences such that they bind specifically within the conserved sequences and amplify a DNA-fragment having a length of 846 bp. Standard plasmids pCR1+11 and pCR1-8 were obtained by inserting inbetween the NcoI and SacI sites of the pBluescript vector, synthetic oligonucleotides containing the CR1-derived sequence from position 260 to 345 (according to Stumph et al., 1981, Nucl. Acid. Res. 9: 5383–5397). For pCR1+11, the CR1 sequence contains an insertion of 11 nucleotides and for the standard plasmid pCR1-8 a deletion of 8 nucleotides at position 302 (according to Stumph et al.). Therefore, the PCR products derived from these standard plasmids are 95 bp and 76 bp in length.

The results of the HSV DNA and CEC DNA quantitation are summarized in Table 6.

TABLE 6

Quantitation of HSV-1 and CEC Nucleic Acid
prior to and after Disintegration by Methylene
Blue/Laser Treatment or Formalin Inactivation of a HSV
Subunit Vaccine

| | DNA Content (pg/ml) | |
|---|---|---|
| | CEC DNA | HSV DNA |
| Starting Material | 95 | 66 |
| 30 Cycles Laser/MB | <1 | <1 |
| Formalin | 88 | 48 |

Example 7

Comparison of the Disintegration of Vero cell DNA by Methylene Blue/Laser Beam and Formalin Treatment An HIV-1 gp160 candidate vaccine was purified from recombinant vaccinia infected Vero cells. This was carried out by extraction with deoxycholate followed by lentil-lectin and immunoaffinity chromatography as described in Barrett et al. (AIDS Res. Human Retrov. 5 (1989) 159–171).

This preparation was then subjected to formalin inactivation (30 h, 0.05% end-concentration of formalin, 37° C.) or was subjected to 30 cycles of methylene blue/laser beam treatment with a methylene blue end concentration of 2 μM as described in Example 1. The Vero cell DNA content of the starting material and following inactivation by formalin and methylene blue/laser beam treatment was determined by using primers:

Alu A2/2 (SEQ ID NO:7): GCCGGGCGTAGTG-GCGGGCGCCTGTAGT and

Alu B (SEQ ID NO:8): GAGACAGAGTCTCGCTCT-GTCGCCCAGG which bind in a highly conserved region in the so-called "Alu repeat" sequences and amplify a 146 bp fragment (Jelinek et al., Ann. Rev. Biochem. 51 (1982) 813–844).

The standard plasmid pAlu20 is derived from the plasmid pAlu-wt, which consists of the known pCRII plasmid (of InVitrogen) and an insert at the multiple cloning site of the PCRII plasmid, which insert contains the bp 148 to 294 of the Alu-repeat-specific sequence from Batzer et al. (1990. Nucl. Acid Res. 18:6793–6798). In pAlu20, the bp 178 to 197 were deleted.

The lengths of the PCR products of standard pAlu2O and wildtype DNA thus are 126 and 146 bp, respectively.

The results of DNA quantitation prior to and after disintegration are summarized in Table 7.

TABLE 7

Disintegration of Vero Cell DNA by Methylene
Blue/Laser Beam Treatment in a Recombinant HIV-1 GP160
Vaccine

| | DNA Content (pg/ml) |
|---|---|
| Starting material | 76 |
| 30 Cycles Laser/MB | <10 |
| Formalin | 69 |

Example 8

Effect of Methylene Blue/Laser Beam Treatment on Recombinant FVIII-Derived Cell Culture A cell culture of recombinant CHO cells transfected with cDNA encoding FVIII-activity was spiked with an ecotropic murine retrovirus MuLV strain and methylene blue was added to give an end concentration of 2 µM. This was then subjected to 10, 20 and 30 cycles laser beam treatment as described in Example 1. Virus titre and FVIII activity were determined before addition of methylene blue and after 10, 20 and 30 cycles laser beam treatment. Virus titre was determined using the XC plaque assay as described by Hartley et al. (1975, Virology 65, 128–134) and FVIII activity was determined according to the chromogenic method as described in the instructions for the Immunochrom® reagent kit.

The results summarized in Table 8 show that virus is efficiently inactivated after 10 cycles of laser beam irradiation in the presence of 2 µM methylene blue. Under these conditions the FVIII activity is essentially unaltered.

TABLE 8

Inactivation of MuLV by Methylene Blue/Laser Beam Treatment in a rFVIII Preparation and Determination of rFVIII Activity

| MB/Laser Beam Cycles | FVIII Activity (Units/ml) | MuLV Titre (FFU/ml) |
| --- | --- | --- |
| 0 | 21.7 | $10^{5.4}$ |
| 10 | 20.3 | $<10^0$ |
| 20 | 15.9 | $<10^0$ |
| 30 | 15.4 | $<10^0$ |

Example 9

Effect of Methylene Blue/Laser Beam Treatment on Recombinant vWF Derived from Cell Culture A supernatant from a Chinese hamster ovary (CHO) cell culture expressing recombinant vWF was subjected to methylene blue/laser beam treatment as described for. rFVIII Example 8. Samples were drawn for RistoCo:F activity and vWF antigen determination before addition of methylene blue and after 10, 20 and 30 cycles of laser beam/methylene blue treatment. Results are summarized in Table 9.

TABLE 9

RistoCO:F Activity of rvWF after Methylene Blue/Laser Treatment

| MB/Laser Light Cycles | RistoCO:F/vWF Ag |
| --- | --- |
| 0 | 17.8 |
| 10 | 17.6 |
| 20 | 15.5 |
| 30 | 15.4 |

Example 10

Oncogene Disintegration by Methylene Blue/Laser Beam Treatment

Oncogene activation resulting in thymic lymphoma in C57 B1/6J mice was induced by i.p. injection of the chemical carcinogen N-nitrosomethylurea (30 mg per kg, once a week for 5 consecutive weeks). High molecular weight DNA containing the induced oncogenes was prepared from thymus tumors by standard techniques. This was prepared at a concentration of 100 µg/ml with 2 µmoles/ml methylene blue and inactivated by 30 cycles exposure to laser light beam at 632 nm with an intensity of 10 mW. Control preparations without methylene blue were treated identically. The tumorogenicity of both preparations was analysed by transfection-transformation assays on NIH/3T3 cells. These cells were transfected with methylene blue/laser beam disintegrated and control DNA using the $CaPO_4$ precipitation method. The precipitated DNA was mixed with tissue culture medium and placed into plastic petri dishes containing NIH/3T3 cells (25 µg DNA to $5 \times 10^5$ cells). After subculturing and 20 day incubation, multiple large foci composed of morphologically transformed cells were observed and counted in a total of ten plates for each DNA preparation.

TABLE 10

Determination of Oncogenicity of DNA prior to and after Laser Treatment and Methylene Blue/Laser Treatment

| Oncogene DNA Preparation | Number of Foci of Transformed Cells |
| --- | --- |
| Non-Treated Control | 109 |
| Laser-Beam Treated without Methylene Blue | 79 |
| Methylene Blue Treated without Laser Beam | 86 |
| Laser Beam with Methylene Blue Treatment | 4 |

Example 11

Oncogene Disintegration by Laser Beam Treatment

High molecular weight DNA containing induced oncogenes were prepared as described in Example 10 and disintegrated by 30 cycles of exposure to laser beam at 320 nm with an intensity of 10 mW. Tumorgenicity of the preparation was analysed as described in Example 11.

TABLE 11

Determination of Oncogenicity of DNA prior to and after Laser Treatment at 320 nm

| Oncogene DNA Preparation | Number of Foci of Transformed Cells |
| --- | --- |
| Non-Treated Control | 109 |
| Laser-Beam Treated without Methylene Blue | 10 |
| Methylene Blue Treated without Laser Beam | 86 |
| Laser Beam with Methylene Blue Treatment | 10 |

Example 12

Inactivation of Murine Retroviruses in a Monoclonal Antibody Containing Hybridoma Supernatant An ecotropic murine retrovirus, MuLV strain SN-E81, was added to a hybridoma supernatant containing a monoclonal antibody directed against HIV-1 gp160. Methylene blue was added to the supernatant to an end-concentration of 2 µM and the mixture was subjected to 10, 20 and 30 cycles laser beam treatment as described above. The virus and antibody titre was determined before addition of methylene blue and after 10, 20 and 30 cycles laser beam treatment. Virus titre was determined using the XC focus forming assay as described by Hartley et al., 1975. Virology 65, 128–134. The antibody titre was determined by standard ELISA techniques using recombinant gp160 coated plates. Briefly, microtitre plates were coated with 0.5 µg purified recombinant HIV-1 gp160 using 100 µl per well. Sera were serially two fold diluted and 100 μl of each dilution were added to the precoated plates and incubated at 37° C. for 1 hour. After extensive washing each well was filled with 100 μl of horseradish peroxidase conjugated anti-mouse IgG and incubated at 37° C. for 1 hour. After washing, 200 μl of activated substrate (O-phenylenediamine hydrochloride) were added to each well and incubated at room temperature in the dark for 10 minutes. The reaction was stopped by the addition of 50 μl 5M sulphuric acid and the absorbance was read at 490 nm. The antibody titre was determined as the reciprocal of the highest dilution which gave a positive reaction.

The results are summarized in Table 12.

TABLE 12

MuLV Titre and Antibody Titre after Methylene Blue/Laser Treatment

| MB/Laser Beam Cycles | MuLV Titre | Antibody Titre |
|---|---|---|
| 0 | $10^{5.3}$ | 1:5120 |
| 10 | $<10^{0}$ | 1:5120 |
| 20 | $<10^{0}$ | 1:5120 |
| 30 | $<10^{0}$ | 1:2560 |

Example 13

Potency of Formalin and Methylene Blue/Beam light Inactivated TBEV in a Mouse Challenge Model Tick-borne encephalitis virus (TBEV) grown on chicken embryo cells was inactivated either by formalin treatment (0.05% formalin, 37° C. for 30 h) or by methylene blue treatment (30 cycles laser beam with an methylene blue concentration of 2 μM). Both preparations were further purified by sucrose gradient centrifugation followed by dialysis. The samples were diluted to give equal protein concentrations.

The immunogenicity of the preparations was determined by $PD_{50}$ determination followed by adjuvantation with alum. Groups of twenty mice were immunized subcutaneously with three-fold dilutions of the adjuvanted vaccine preparations. One week post immunization the mice were boostered with the same antigen dose. Two weeks after the second immunization mice were challenged by i.p. inoculation with $10^2$ $LD_{50}$ doses of live virus. The mice were then observed for a period of 21 days and the number of surviving mice after this period was recorded. The protective dose for 50% of the mice ($PD_{50}$) was calculated according to the method of Kärber, 1931, Arch.Exp.Pathol.Pharmakol. 162, 480–483 and is shown in Table 13.

TABLE 13

Potency Measurement of Methylene Blue/Laser Beam and Formalin Inactivated TBEV Vaccines

| Vaccine Preparation | $PD_{50}$ (ng) |
|---|---|
| Formalin Inactivated | 32.3 |
| Laser Beam/MB Inactivated | 18.7 |

Example 14

Comparison of the Reactivity of Formalin Inactivated and Methylene Blue/Laser beam Inactivated Tick-Borne Encephalitis Virus with a Panel of Specific Monoclonal Antibodies Tick-borne encephalitis virus was grown on primary chicken embryo cells and purified by two cycles of sucrose density gradient centrifugation. They were then pelleted by ultracentrifugation, resuspended in 10 mM Tris-HCl, pH 7.2, and subjected to formalin inactivation (0.05% formalin end-concentration, 30 h at 37° C.) or methylene blue/laser beam inactivation (2 μM methylene blue end concentration, ten cycles). Both preparations were then subjected to Sephadex 6-25 chromatography and following elution, they were adjusted to give equal protein concentrations.

The reactivities of both preparations with eight different monoclonal antibodies directed against the TBEV glycoprotein were determined by standard ELISA techniques. Microtitre plates were coated with the virus preparation at a concentration of 2 μg/ml in carbonate buffer, pH 9.6. Following washing the monoclonals were added and allowed to react for 1 hour at 37° C. Horseradish peroxidase conjugated anti-mouse immunoglobulin was then added and following incubation for one hour at 37° C. and washing, substrate was added and the absorbance at 492 nm was measured after stopping the reaction by the addition of 2N $H_2SO_4$. All monoclonals demonstrated a higher reactivity with the methylene blue/laser beam inactivated virus preparation than with the formalin inactivated vaccine preparation. The results are summurized in Table 14.

TABLE 14

ELISA Absorbance Values of Monoclonal Antibodies Tested Against Formalin and Methylene Blue/Laser Beam Inactivated Tick-borne Encephalitis Virus

| Inactivation Method | Monoclonal Antibody | | | | | | | |
|---|---|---|---|---|---|---|---|---|
| | 8H6 | 6E1 | 2B5 | 3C7 | 2B6 | 5F6 | 1C2 | 4A5 |
| Formalin | 0.46 | 0.45 | 0.46 | 0.62 | 1.21 | 0.10 | 0.34 | 0.47 |
| Methylene Blue/ Laser Beam | 0.57 | 0.61 | 0.62 | 0.81 | 1.92 | 1.35 | 0.82 | 0.98 |

Example 15

Disintegration of Nucleic Acid of Prokaryotic Pathogen by Methylene Blue/Laser Beam Treatment A culture of B. burgdorferi cells were grown to a cell count of $1 \times 10^7$ spirochaetes/ml and methylene blue was added to a final concentration of 2 μM. The culture was subjected to 30 cycles of laser beam treatment. The presence of B. burgdorferi DNA prior to and after methylene blue/laser treatment was determined by PCR amplification using the primers

LD1 (SEQ ID NO:9): ATG CAC ACT TGG TGT TAA CTA

LD2 (SEQ ID NO:10): GAC TTA TCA CCG GCA GTC TTA (according to Marconi et al., 1992, J. Clin. Microbiol. 30: 2830–2834)

Example 16

Inactivation of Parvovirus in a Human Plasma derived Product by Methylene Blue/Laser Beam Treatment A highly purified FVIII concentrate solution was spiked with the Parvovirus, Minute Virus of Mice (MVM) and methylene blue was added to give an end concentration of 30 μM. This was then subjected to 10, 20 and 30 cycles of laser beam treatment as described in Example 1. Virus titres and FVIII activity were determined before addition of methylene blue and after 10, 20 and 30 cycles laser beam treatment. Virus titre was measured by means of $TCID_{50}$ determination (Reed et al., 1938, Amer.J.Hyg. 27:493–497) using A9 cells (ATCC CRL 6319) and FVIII activity was determined according to the chromogenic method as described in the instructions for the Immunochrom reagent kit.

The results summarized in Table 15 show that almost 5 logs MVM are inactivated following 30 cycles of laser beam/methylene blue treatment. Under these conditions more than 50% FVIII activity is retained.

TABLE 15

Inactivation of MVM Parvovirus in FVIII Concentrate by Methylene Blue/Laser Beam Treatment

| Laser Beam Cycles | MVM Titre ($TCID_{50}$/ml) | FVIII Activity (Units/ml) |
|---|---|---|
| 0 | $10^{7.2}$ | 49.7 |
| 10 | $10^{5.2}$ | 41.6 |
| 20 | $10^{3.6}$ | 31.8 |
| 30 | $10^{2.5}$ | 25.6 |

Example 17

Disintegration of Nucleic Acid of B19 Parvovirus by Methylene Blue/Laser Treatment and Detection of Disintegration A plasma preparation was spiked with a high-titre virus stock solution of human parvovirus B19. To this mixture, methylene blue was added to an end concentration of 30 $\mu$M. After extensive washing of the solution, the material was pumped through a tube of stainless steel comprising a glass window having a diameter of 2×2 mm at a flow rate of 4 ml/min. The glass window was simultaneously irradiated with a laser beam of a He-Ne laser at a wave length of 633 nm and a laser output of 10 mW. The material was irradiated betwen 0 and 50 cycles, and the B19 parvovirus DNA was quantitated in samples by means of PCR after 0, 1, 5, 10, 20, 30, 40 and 50 cycles. As the control, a mixture containing methylene blue, yet not irradiated with laser light, was used. The results of the quantitative determination of the B19-specific DNA copy number are summarized in Table 16. The results show that after approximately 40 cycles with methylene blue/laser light treatment, the content of B19-specific DNA had been reduced to below the detection limit of the measuring system.

TABLE 16

Disintegration of Parvovirus B19 DNA by means of Methylene Blue/Laser Beam Treatment and Determination of the DNA Copy Number prior to and following Treatment

| Treatment | B19 DNA Copy Number per ml |
|---|---|
| None | $10^{11.4}$ |
| 1 × Cycle MB/Laser | $10^{9.6}$ |
| 5 × Cycles MB/Laser | $10^{7.8}$ |
| 10 × Cycles MB/Laser | $10^{6.0}$ |
| 20 × Cycles MB/Laser | $10^{4.6}$ |
| 30 × Cycles MB/Laser | $10^{3.0}$ |
| 40 × Cycles MB/Laser | $<10^{2.7}$ |
| 50 × Cycles MB/Laser | $<10^{2.7}$ |
| 50 × Cycles with MB without Laser | $10^{8.9}$ |

We claim:

1. A method for disintegrating nucleic acids in a biologically active proteinaceous material that has biological integrity, comprising admixing a phenothiazine photodynamic substance to the biologically active material to form a mixture, and exposing the mixture to at least one cycle of irradiation with laser beam light having an intensity of $\leq 0.1$ J/cm$^2$ per cycle in order to (i) reduce nucleic acid template activity in the biologically active material by at least a factor of 7 log steps and/or (ii) to reduce the nucleic acid content to less than 100 pg/ml, thereby disintegrating and/or inactivating substantially all biologically active nucleic acid contained in the biologically active material while substantially retaining the biological integrity and activity of the biologically active material.

2. The method according to claim 1, wherein the nucleic acid content is reduced to less than 10 pg/ml.

3. The method according to claim 1, wherein the nucleic acid content is reduced to less than 1 pg/ml.

4. The method according to claim 1, further comprising quantitating the nucleic acids in order to determine the level inactivation and/or disintegration of the biologically active nucleic acid in order to obtain a biological material having a quantitated nucleic acid content of less than 100 pg per dose.

5. The method according to claim 4, wherein the quantitated nucleic acid content of the biological material obtained is less than 10 pg per dose.

6. The method according to claim 4, wherein the quantitated nucleic acid content of the biological material obtained is less than 1 pg per dose.

7. The method according to claim 4, wherein the quantitated nucleic acid content of the biological material obtained is 1 to 500 copies/ml.

8. The method according to claim 1, wherein the phenothiazine photodynamic substance is selected from the group consisting of methylene blue, toluidine blue or azur B.

9. The method according to claim 1, wherein the phenothiazine photodynamic substance is present at a concentration of between 0.01 $\mu$M and 50 $\mu$M.

10. The method according to claim 1, wherein the phenothiazine photodynamic substance is present at a concentration of between 1 $\mu$M and 40 $\mu$M.

11. The method according to claim 1, wherein the laser beam has a wave length in the range of the maximum activation rate of the photodynamic substance.

12. The method according to claim 1, wherein the wave length of the laser beam is between 600 and 680 nm.

13. The method according to claim 1, wherein the laser light has an intensity of $\leq 0.08$ J/cm$^2$.

14. The method according to claim 1, wherein the laser light has an intensity of ≦0.06 J/cm².

15. The method according to claim 1, further comprising admixing at least one selected from the group consisting of a stabilizer, a quencher and a scavenger to the mixture before the mixture is exposed to the irradiation with laser beam light.

16. The method according to claim 15, wherein the stabilizer is selected from the group consisting of sugar, polyalcohol, amino acids, peptides and carboxylic acids, and the quencher and scavenger are selected from the group consisting of mannitol, glycerol, reduced glutathione and superoxide dismutase.

17. The method according to claim 1, wherein at least one selected from the group consisting of a quencher, a scavenger and a stabilizer is admixed to the biologically active proteinaceous material prior to admixing the phenothiazine photodynamic substance.

18. The method according to claim 4, wherein the process for quantitating nucleic acids is a nucleic acid amplification process comprising admixing an amount of at least one known nucleic acid molecule as an internal standard to the biological material prior to carrying out an amplification step, wherein the standard molecule differs from the nucleic acid to be quantitated by at least one detectable characteristic.

19. The method according to claim 1, wherein the biologically active material comprises at least one selected from the group consisting of a blood factor, a genetically engineered proteinaceous product, a microbigical pathogen, a molecular pathogen and any part of the foregoing.

20. The method according to claim 1, wherein the biologically active material is selected from the group consisting of a cell culture, a cell suspension, a cell layer, a cell culture supernatant and a broken-up cell preparation obtained from infected, transfected or transformed cells.

21. The method according to claim 1, wherein the biologically active nucleic acid is selected from the group consisting of DNA, RNA, a genome and any part of the foregoing.

22. The method according to claim 21, wherein the biologically active nucleic acid is a gene.

23. The method according to claim 1, wherein the biologically active nucleic acid has a nucleic acid template activity and includes a sequence for primer and polymerase binding, and wherein the biologically active nucleic acid is amplifiable.

24. The method according to claim 1, wherein the biologically active nucleic acid is obtained from a eukaryotic source.

25. The method according to claim 24, wherein the eukaryotic source is selected from the group consisting of a vertebrate cell, a tumor cell line, an oncogene, a protooncogene and a hybridoma cell line.

26. The method according to claim 1, wherein the biologically active nucleic acid is derived from a microorganism selected from the group consisting of a protozoon, a bacterium, a virus, a microbiological pathogen, a molecular pathogen any part of the foregoing.

27. A method of inactivating viruses comprising
admixing a phenothiazine photodynamic substance to a virus-containing biological material to thereby form a mixture, and
exposing the mixture to at least one cycle of irradiation with laser beam light having an intensity of <0.1 J/cm² per cycle in order to (i) reduce nucleic acid template activity in the biologically active material by at least a factor of 7 log steps and/or (ii) to reduce the nucleic acid content to less than 100 pg/ml, thereby disintegrating and/or inactivating substantially all biologically active nucleic acid contained in the biologically active material while substantially retaining the biological integrity and activity of the biologically active material.

28. The method according to claim 27, wherein the nucleic acid content is reduced to <10 pg/ml.

29. The method according to claim 27, wherein the nucleic acid content is reduced to <1 pg/ml.

30. The method according to claim 27, wherein the virus is selected from the group consisting of lipid-enveloped viruses, non-lipid-enveloped viruses, DNA viruses, RNA viruses and attenuated viruses.

31. The method according to claim 30, wherein the virus is selected from the group consisting of adenovirus, herpes virus, papovavirus, poxvirus, parvovirus, reovirus, retrovirus, myxovirus, paramyxovirus, picornavirus, Toga virus, flavivirus, orthomyxovirus and rhabdovirus.

32. The method according to claim 31, wherein the virus is selected from the group consisting of influenza virus, HIV, HCV, HAV, HBV, TBEV and CMV.

33. The method according to claim 30, wherein the virus is attenuated.

34. A method of inactivating non-enveloped viruses in a proteinaceous biological material that has biological integrity, comprising
admixing a phenothiazine photodynamic substance at a concentration of at least 20 μM to a biological material in order to form a mixture, and
exposing the mixture to at least 20 cycles of irradiation with a laser beam light in the range of the maximum activation rate of the phenothiazine photodynamic substance, wherein the laser beam light has a light intensity of <0.1 J/cm² per cycle.

35. The method according to claim 34, wherein the light intensity of the laser beam light is ≦0.06 J/cm² per cycle.

36. The method according to claim 34, wherein the non-enveloped viruses to be inactivated are selected from the group consisting of picornaviruses and parvoviruses.

37. The method according to claim 34, wherein the proteinaceous biological material comprises infectious nucleic acid, and wherein substantially all of the biologically active infectious nucleic acid is disintegrated and/or inactivated while retaining biological integrity and activity of the proteinaceous biological material.

38. The method according to claim 37, further comprising quantitating the nucleic acids in order to determine the level inactivation and/or disintegration of the biologically active nucleic acid in order to obtain a biological material having a quantitated nucleic acid content of less than 100 pg per dose.

39. The method according to claim 38, wherein the quantitated nucleic acid content is less than 10 pg per dose.

40. The method according to claim 38, wherein the quantitated nucleic acid content is less than 1 pg per dose.

41. The method according to claim 38, wherein the quantitated nucleic acid content is 1 to 500 copies/ml.

42. A virus-inactivated biological material obtainable by inactivating non-lipid-enveloped viruses in a proteinaceous biological material that has biological integrity, wherein the inactivation comprises
admixing a phenothiazine photodynamic substance to a non-lipid-enveloped virus-containing biological material to thereby form a mixture, and
exposing the mixture to at least one cycle of irradiation with laser beam light having an intensity of ≦0.1

J/cm² per cycle in order to (i) reduce nucleic acid template activity in the biologically active material by at least a factor of 7 log steps and/or (ii) to reduce the nucleic acid content to less than 100 pg/ml, thereby disintegrating and/or inactivating substantially all biologically active nucleic acid contained in the biologically active material while substantially retaining the biological integrity and activity of biologically active material.

43. An inactivated virus vaccine obtainable by inactivation of viruses in a proteinaceous biological material that has biological integrity, wherein the inactivation comprises admixing a phenothiazine photodynamic substance at a concentration of at least 20 μM to the proteinaceous biological material in order to form a mixture, and exposing the mixture to at least 20 cycles of irradiation with a laser beam light in the range of the maximum activation rate of the phenothiazine photodynamic substance, wherein the laser beam light has a light intensity of ≦0.1 J/cm² per cycle.

44. A method of producing an inactivated virus vaccine, comprising admixing a phenothiazine photodynamic substance to a virus-containing biological material to thereby form a mixture, exposing the mixture to irradiation with laser beam light having an intensity of ≦0.1 J/cm² per cycle to disintegrate and/or inactivate substantially all biologically active nucleic acid contained in the viruses of the biological material while substantially retaining the antigenicity and immunogenicity of the virus, quantitating the nucleic acids in order to determine the level inactivation and/or disintegration of the biologically active nucleic acid in order to obtain a biological material having a quantitated nucleic acid content of less than 100 pg per dose, and formulating the inactivated viruses with a physiologically acceptable carrier in order to make the virus vaccine.

45. The method according to claim 44, wherein the quantitated nucleic acid content of the virus-containing material obtained is less than 10 pg per dose.

46. The method according to claim 44, wherein the quantitated nucleic acid content of the virus-containing biologically active material obtained is less than 1 pg per dose.

47. The method according to claim 44, wherein the quantitated nucleic acid content of the virus-containing biologically active material obtained is 1 to 500 copies/ml.

48. The method according to claim 44, further comprising subjecting the inactivated viruses to further purification before formulating the inactivated viruses with a physiologically acceptable carrier.

49. The method according to claim 44, wherein the virus is a viral pathogen selected from the group consisting of lipid-enveloped and non-lipid-enveloped viruses.

50. The method according to claim 44, wherein the virus is a viral pathogen selected from the group of DNA containing viruses and RNA containing viruses.

51. The method according to claim 44, wherein the virus is a viral pathogen selected from the group consisting of adenovirus, herpes virus, papova virus, poxvirus, parvovirus, reovirus, retrovirus, myxovirus, paramyxovirus, picornavirus, Toga virus, flavivirus, orthomyxovirus and rhabdovirus.

52. The method according to claim 44, wherein the virus is a viral pathogen selected from the group consisting of influenza virus, HIV, HCV, HAV, HBV, TBEV and CMV.

53. The method according to claim 44, wherein the virus is attenuated.

54. The method according to claim 44, wherein the virus-containing material is obtainable from a culture of virus-infected cells, a culture supernatant of virus-infected cells, a cell component of virus-infected cells or from a purified-virus-containing solution.

55. The method according to claim 54, wherein the virus-infected cells are vertebrate cells.

56. The method according to claim 55, wherein the vertebrate cells are selected from the group consisting of chicken embryo cells, VERO cells, CV-1 cells, LLC-MK-2 cells, MDCK cells, MDBK cells, WI-38 cells and MRC-5 cells.

57. The method according to claim 44, wherein the nucleic acid is derived from at least one selected from the group consisting of the cell and the virus.

58. The method according to claim 42, wherein the laser beam light has an intensity of ≦0.08 J/cm² per cycle.

59. The method according to claim 43, wherein the laser beam light has an intensity of ≦0.08 J/cm² per cycle.

60. The method according to claim 44, wherein the laser beam light has an intensity of ≦0.08 J/cm² per cycle.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Primer"

(xi) SEQUENCE DESCRIPTION: SEQ ID NO:1:

ATAATCCACC TATCCCAGTA GGAGAAAT        28

(2) INFORMATION FOR SEQ ID NO:2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Primer"

(xi) SEQUENCE DESCRIPTION: SEQ ID NO:2:

TTTGGTCCTT GTCTTATGTC CAGAATGC        28

```
(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:3:

AACTACCCCG ATCATCAG                                                    18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:4:

AGGCCCACTT AGACGACA                                                    18

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:5:

ATGAGGCACT GGAACAGGTT GCCC                                             24

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:6:

AGGGCCACAT CCAGCCTGG                                                   19

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:7:

GCCGGGCGTA GTGGCGGGCG CCTGTAGT                                         28
```

-continued (2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:8:

GAGACAGAGT CTCGCTCTGT CGCCCAGG                                      28

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:9:

ATGCACACTT GGTGTTAACT A                                           21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:10:

GACTTATCAC CGGCAGTCTT A                                           21